US012193732B2

(12) United States Patent
Panescu et al.

(10) Patent No.: US 12,193,732 B2
(45) Date of Patent: *Jan. 14, 2025

(54) ABLATION CATHETER AND OPERATION METHOD OF SAME

(71) Applicant: CRC EP, Inc., Lake Oswego, OR (US)

(72) Inventors: Dorin Panescu, San Jose, CA (US); Cary Hata, Irvine, CA (US); Alan De La Rama, Cerritos, CA (US); Henning Ebert, Berlin (DE); Steffen Holzinger, Berlin (DE)

(73) Assignee: CRC EP, INC., Lake Oswego, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,360

(22) Filed: Apr. 18, 2024

(65) Prior Publication Data

US 2024/0261018 A1 Aug. 8, 2024

Related U.S. Application Data

(63) Continuation of application No. 17/563,527, filed on Dec. 28, 2021, now Pat. No. 12,082,877.

(Continued)

(30) Foreign Application Priority Data

May 5, 2021 (EP) .................................... 21172336

(51) Int. Cl.
*A61B 18/12* (2006.01)
*A61B 18/14* (2006.01)
*A61B 18/00* (2006.01)

(52) U.S. Cl.
CPC ...... *A61B 18/1492* (2013.01); *A61B 18/1206* (2013.01); *A61B 2018/00166* (2013.01);
(Continued)

(58) Field of Classification Search
CPC ............ A61B 18/1492; A61B 18/1206; A61B 2018/00166; A61B 2018/00363;
(Continued)

(56) References Cited

U.S. PATENT DOCUMENTS 5,938,694 A * 8/1999 Jaraczewski ........... A61B 5/287
607/122
7,344,533 B2 3/2008 Pearson et al.
(Continued)

FOREIGN PATENT DOCUMENTS

CN 113648055 A 11/2021
WO 2016007851 A1 1/2016
(Continued)

OTHER PUBLICATIONS

Search Report mailed on Oct. 28, 2021 by the European Patent Office for Application No. 21172336.6.
(Continued)

*Primary Examiner* — Daniel W Fowler
(74) *Attorney, Agent, or Firm* — Procopio, Cory, Hargreaves & Savitch LLP

(57) ABSTRACT

The invention relates to an ablation catheter for treatment of a patient's tissue, for example for a PVI procedure on a patient's heart, comprising an elongated catheter shaft and an ablation portion being arranged at a distal end of the catheter shaft with a plurality of electrodes accommodated along the ablation portion, wherein the ablation portion comprises at least two loop sections forming a three-dimensional spiral. In order to increase safety of ablation treatment, spare adjacent tissue (e.g. nerves, vessels, esophagus) and shorten ablation time, a pitch, or clearance of two neighboring loop sections is greater than an ionization threshold of the medium around the distal section, for example blood or gases resulted from electrolysis. The
(Continued)

invention further relates to an operation method of such ablation catheter.

25 Claims, 18 Drawing Sheets

Related U.S. Application Data

(60) Provisional application No. 63/140,390, filed on Jan. 22, 2021.

(52) U.S. Cl.
CPC ............ *A61B 2018/00363* (2013.01); *A61B 2018/00577* (2013.01); *A61B 2018/00839* (2013.01); *A61B 2018/1226* (2013.01); *A61B 2018/1253* (2013.01); *A61B 2018/126* (2013.01); *A61B 2018/1435* (2013.01); *A61B 2018/1467* (2013.01); *A61B 2218/002* (2013.01)

(58) Field of Classification Search
CPC  A61B 2018/00577; A61B 2018/00839; A61B 2018/1226; A61B 2018/1253; A61B 2018/126; A61B 2018/1435; A61B 2018/1467

See application file for complete search history.

(56) References Cited

U.S. PATENT DOCUMENTS

| | | | |
|---|---|---|---|
| 9,265,557 B2 | 2/2016 | Sherman et al. | |
| 9,877,781 B2 | 1/2018 | Grasse et al. | |
| 2002/0111618 A1* | 8/2002 | Stewart | A61B 18/1492 606/41 |
| 2004/0147917 A1 | 7/2004 | Mueller, Jr. | |
| 2007/0219546 A1 | 9/2007 | Mody et al. | |
| 2009/0287202 A1 | 11/2009 | Ingle | |
| 2010/0030299 A1* | 2/2010 | Covalin | A61N 1/0456 607/46 |
| 2012/0220999 A1* | 8/2012 | Long | A61B 18/1477 606/41 |
| 2012/0245577 A1 | 9/2012 | Mihalik | |
| 2013/0184702 A1* | 7/2013 | Neal, II | A61B 18/00 606/41 |
| 2013/0304062 A1 | 11/2013 | Chan et al. | |
| 2014/0031804 A1* | 1/2014 | Lalonde | A61B 18/1492 606/41 |
| 2014/0148805 A1 | 5/2014 | Stewart et al. | |
| 2015/0126992 A1* | 5/2015 | Mogul | A61B 18/1492 606/34 |
| 2016/0008058 A1* | 1/2016 | Hu | A61B 18/02 606/41 |
| 2016/0128771 A1 | 5/2016 | Ditter et al. | |
| 2016/0166310 A1 | 6/2016 | Steward | |
| 2016/0192981 A1 | 7/2016 | Dimmer et al. | |
| 2017/0065343 A1 | 3/2017 | Mickelsen | |
| 2018/0221078 A1* | 8/2018 | Howard | A61B 18/14 |
| 2018/0303543 A1* | 10/2018 | Stewart | A61B 18/1492 |
| 2018/0311497 A1 | 11/2018 | Viswanathan | |
| 2018/0360533 A1 | 12/2018 | Olson | |
| 2019/0030328 A1* | 1/2019 | Stewart | A61B 18/1492 |
| 2019/0307500 A1 | 10/2019 | Byrd et al. | |
| 2020/0138506 A1* | 5/2020 | Fraasch | A61B 18/1233 |
| 2020/0289188 A1* | 9/2020 | Forsyth | A61B 18/1206 |
| 2021/0085205 A1 | 3/2021 | Ditter | |
| 2021/0401491 A1 | 12/2021 | Altmann et al. | |
| 2022/0133403 A1 | 5/2022 | Olson | |

FOREIGN PATENT DOCUMENTS

| | | |
|---|---|---|
| WO | 2018102376 A1 | 6/2018 |
| WO | 2020224972 A1 | 11/2020 |

OTHER PUBLICATIONS

Written Opinion of the International Searching Authority for PCT/US2022/013147, dated Apr. 6, 2022.
International Search Report for PCT/US2022/013255 dated Apr. 6, 2022.
Written Opinion of the International Searching Authority for PCT/US2022/013255 dated Apr. 6, 2022.
International Search Report for PCT/US2022/013245 dated May 5, 2022.
Written Opinion of the International Searching Authority for PCT/US2022/013245 dated May 5, 2022.
International Search Report for PCT/US2022/013147 dated Apr. 6, 2022.

\* cited by examiner

< LIST SWEEP DISP >

MODE :SEQ

| No. | FREQ [Hz] | Z [Ω] | θ [°] | CMP |
|---|---|---|---|---|
| 021 | 100.0 | 222.384 | -39.456 | P |
| 022 | 500.0 | 138.325 | -19.918 | P |
| 023 | 1.000k | 125.914 | -13.266 | P |
| 024 | 5.000k | 115.308 | -4.382 | P |
| 025 | 10.00k | 113.633 | -2.660 | P |
| 026 | 50.00k | 111.877 | -0.654 | P |
| > 027 | 100.0k | 111.807 | -0.123 | P |
| 028 | 250.0k | 111.299 | 0.770 | P |
| 029 | 500.0k | 110.809 | 1.996 | P |
| 030 | 1.000M | 109.941 | 4.403 | P |

MEAS DISPLAY

BIN NO.

BIN COUNT

LIST SWEEP

FIG. 20A

< LIST SWEEP DISP >

MODE :SEQ

| No. | FREQ [Hz] | Z [Ω] | θ [°] | CMP |
|---|---|---|---|---|
| ∨ 021 | 100.0 | 3.69379 | 0.040 | P |
| 022 | 500.0 | 3.69453 | 0.143 | P |
| 023 | 1.000k | 3.42997 | -0.463 | P |
| 024 | 5.000k | 3.69596 | 1.398 | P |
| 025 | 10.00k | 3.69991 | 2.802 | P |
| 026 | 50.00k | 3.80927 | 13.673 | P |
| 027 | 100.0k | 4.12570 | 25.810 | P |
| 028 | 250.0k | 5.84276 | 49.811 | P |
| 029 | 500.0k | 9.69114 | 66.147 | P |
| 030 | 1.000M | 17.9946 | 75.743 | P |

MEAS DISPLAY

BIN NO.

BIN COUNT

LIST SWEEP

FIG. 20B

ABLATION CATHETER AND OPERATION METHOD OF SAME

CROSS-REFERENCE TO RELATED APPLICATIONS

The present application is a continuation of U.S. patent application Ser. No. 17/563,527 filed Dec. 28, 2021, which claims the benefit of and priority to European Patent Application No. EP 21172336.6 filed May 5, 2021, and claims the benefit of and priority to U.S. Provisional Patent Application No. 63/140,390 filed Jan. 22, 2021, each of which is hereby incorporated by reference in its entirety.

TECHNICAL FIELD

The present invention relates to embodiments of an ablation catheter suitable for pulsed-field ablation (PFA). In particular, the present invention relates to embodiments of a PFA catheter that may be used for safely performing cardiac ablation procedures, such as, but not limited to, pulmonary vein isolation (PVI), persistent atrial fibrillation ablation, ventricular tachycardiac ablation. The catheter comprises multiple electrodes and delivers pulsed-field energy to achieve irreversible electroporation of cardiac tissue.

BACKGROUND

It is known to use ablation catheters for PVI procedures in the therapy of atrial fibrillation (AF) patients. In such procedures, the pulmonary veins (PV) are electrically isolated from the left atrium by creating contiguous circumferential ablation lesions around the pulmonary vein ostium (PVO) or around their antrum. Thus, irregular atrial contractions can be avoided by hindering undesired perturbing electrical signals generated within the PV from propagating into the left atrium. Ablation catheters may be used to deliver therapy to other tissues, such as, but not limited to: ventricles, right atrium, the body of the left atrium, etc. Additionally, other organs may be treated via use of catheters: lungs, liver, kidneys, etc.

Several types of ablation catheters are available including single point tip electrode catheters, circular multi-electrode loop catheters, and balloon-based ablation catheters using different energy sources. They all lack the ability of producing ablations, which safely electrically isolate the arrhythmogenic triggers from the rest of the heart chamber, in a 'one-shot' modality, without further repositioning, rotating or moving of the catheter.

The present disclosure is directed toward overcoming one or more of the above-mentioned problems, though not necessarily limited to embodiments that do.

SUMMARY

It is desirable to further improve ablation treatment by offering catheters and systems which safely achieve a 'moat' of electrical isolation in one shot. The concept of a moat of electrical isolation is defined as region of cardiac tissue that surrounds the arrhythmogenic trigger and prevents its propagation to the rest of the heart chamber. For example, without limitation, referring to situations when the arrhythmogenic triggers reside inside a pulmonary vein, an ablation region which completely renders non-viable the tissue located at the vein ostium or antrum, securing transmurality, would represent said moat of electrical isolation. Given that the tissue within the moat is non-viable, excitation originating from triggers within the corresponding pulmonary vein would not conduct to the rest of the left atrium. Such arrhythmogenic excitation would be blocked by the moat and would not capture the body of the left atrium. In the case of atrial fibrillation, if said moat of conduction block was achieved, triggering mechanisms would be eliminated or reduced in frequency of occurrence. Technologies available today achieve said moats of conduction block, or of electrical isolation, by point-by-point (i.e. catheter repositioned in sequential steps), by rotation (i.e. catheter active element is rotated to completed the moat) or by repositioning (i.e. catheter active element is repositioned to a neighboring location to complete the moat). In other words, prior-art technologies achieve said moat of conduction block by employing 'multiple shots.' While it might be possible to achieve said moat of conduction block in one shot by overpowering the targeted tissue, by doing so collateral organs (e.g. esophagus, lungs, diaphragm, etc.) would be irreversibly damaged. In certain case, these adverse events may pose critical danger to patients. For example, when prior-art technologies overpower structures of the left atrium they may cause atrial-esophageal fistulas. If discovered too late, fistulas may be fatal. Pulsed-field ablation, if designed appropriately, may have the advantage of creating these conduction block/electrical isolation moats in one shot, safely without or with minimal collateral tissue damage.

At least the above problem is solved by an ablation catheter with the features of claim 1, and an operation method of such ablation catheter with the features of claim 11.

In particular, an embodiment of an ablation catheter for treatment of a patient's tissue, for example for a PVI procedure at a patient's heart tissue or vein tissue, comprises an elongated catheter shaft and an ablation portion being arranged at a distal end of the catheter shaft with a plurality of electrodes accommodated along the ablation portion, wherein the ablation portion comprises at least two loop sections forming a three-dimensional spiral, wherein a pitch and/or clearance of two neighboring loop sections is greater than an ionization threshold. Catheters employing loop sections or loop segments include, and are not limited to, catheters with continuous or contiguous spirals. Pulsed-field ablation use high-intensity electrical fields. If catheters are not designed appropriately, the field intensity can be sufficiently high to ionize the medium between electrodes. Under such circumstances, arcing develops. Arcing presents increased levels of danger to patients, as it results in unintended tissue damage. Furthermore, the high temperatures of arcs may melt catheter materials, leaving foreign particles in the patient's blood stream. Therefore, it is important to use catheters designed to prevent ionization from occurring. This can be achieved by design elements that keep the catheter electrodes at distances greater than an amount known or expected to trigger ionization (i.e. ionization threshold).

Within the frame of this application, the phrase "ionization threshold" is understood as a field intensity sufficient to ionize the medium between electrodes in a way arcing develops.

Within the frame of this application, the phrase "at least two loop sections forming a three-dimensional spiral" is understood as a structure comprising at least two loop sections arranged in a way that a three-dimensional spiral is formed. The at least two loop sections could be arranged as a continuous or discontinuous spiral. The beginning and the end of each loop section could be arranged either in the same or in a different plane with respect to the central axis of the three-dimensional spiral. In addition, the at least two loop sections itself could be arranged either in the same or in a different plane with respect to the central axis of the three-dimensional spiral. An example of at least two loop sections forming a continuous spiral is shown in FIG. 1, whereby the beginning and the end of each loop section is arranged in a different plane with respect to the central axis of the three-dimensional axis and whereby the at least two loops are arranged in different planes with respect to the three-dimensional axis.

Within the frame of this application, the pitch of two neighboring loop sections (or loop/spiral arms in the case of a continuous loop/spiral) is defined as the distance of the outer opposite surfaces of the loop section of each of the two neighboring loop sections, wherein the distance is measured perpendicular to the direction of the tangents local to the respective section between which the distance is measured. The pitch is determined in a stage of the catheter, wherein the three-dimensional form of the ablation portion comprising the least two loop sections is not restricted by any external force.

Within the frame of this application, the clearance of two neighboring loop sections is defined in the same way as the pitch measured in a stage of the catheter, wherein the three-dimensional form of the ablation portion comprising the least two loop sections is flattened or almost flattened by external force, e.g. when the catheter is compressed against tissue as shown in FIG. 18B. The at least two loop sections are in the same plane with respect to the central axis of the three-dimensional spiral, if the ablation portion is flattened by external forces.

In accordance with an embodiment, the ablation catheter is configured for delivering pulsed-field ablating (PFA) energy to atrial or ventricular tissue via the ablation electrodes. In other words, the ablation catheter may be configured for carrying out PFA. In particular, the ablation catheter may be used to provide cardiac catheter ablation to treat a variety of cardiac arrhythmias including AF. For example, the ablation catheter may be configured for being connected to a multi-channel PF energy generator which is configured for delivering PF energy. The waveform of said PF energy generator is conceived so that, in conjunction with catheter loop design, achieves intended therapeutic effect while minimizing or reducing chances of ionization. The inventive catheter may also be used for different type of tissue, for example, but not limited to, veins, lungs, liver, kidneys, etc. It may be used for pulmonary vein isolation (PVI), persistent atrial fibrillation ablation, ventricular tachycardiac ablation and other ablation procedures.

The catheter shaft may comprise a handle at its proximal end. Each electrode at the ablation portion is electrically connected via one electrode lead to a power supply and a pulse generator provided at the proximal end of the catheter shaft. Further, the catheter may comprise an electronic control unit (ECU) for controlling ablation procedure and/or processing measurement data. In another embodiment, there are two electrode leads provided at the proximal end and the middle section of the catheter shaft. At the proximal end the first electrode lead is connected to the first group of electrodes and the second electrode lead is connected to the second group of electrodes in order to reduce the diameter of the catheter shaft. The electrode may have a length along the respective loop section of 1 mm to 10 mm, preferably 3 mm to 5 mm. The catheter shaft size may be compatible with a 7 F to 14 F ID sheath, preferable with an 8.5 F ID sheath. The width between neighboring electrodes along the respective loop section may be chosen between 1 mm and 10 mm, preferably 3-6 mm, in order to provide a contiguous ablated area at the patient's tissue.

In an embodiment, the pitch of two neighboring loop sections is further less than a therapeutic threshold of the respective tissue. The therapeutic threshold of the respective tissue is understood as distance known or expected to achieve a continuous moat.

The pitch and/or clearance of a first set of two neighboring loop sections may be different or equal to the pitch and/or clearance of a second set of two neighboring loop sections. Again, the description and disclosure applies equally to catheter designs employing continuous or contiguous loop or spiral structures.

The inventive ablation catheter using PFA is intended to render tissues non-viable by irreversible electroporation (IRE). During IRE the electric field provided by the electrodes accommodated at the neighboring loop sections creates pores in cardiac cell membranes. When the number of pores and their sizes are sufficiently great IRE occurs and the cell programs itself to die. For that neighboring loop sections of the ablation portion form a so-called ablation area. In order to provide proper treatment which causes IRE in the ablation area, the pitch and/or clearance of two neighboring loop sections need to be greater than the ionization threshold in order to avoid ionization and hence scarring. Further, if the pitch and/or clearance is chosen less than the therapeutic threshold the created electric field causes forming of pores reliably. The additional benefit of adaption of loop section pitch to the above-mentioned thresholds is that safety of PFA treatment is increased and adjacent tissue (e.g. nerves, vessels, esophagus) is spared so that the heart's normal pumping performance is not affected. If the loop sections or spiral arms are appropriately sized for deployment at targeted regions, the moat of conduction block can then be achieved in one shot. As a result, the ablation time is shortened.

In an embodiment, in particular with regard to a body fluid (e.g. blood), vascular and/or atrial tissue, the ionization threshold is 2 mm. In a further embodiment, also in particular with regard to vascular and/or atrial tissue, the therapeutic threshold is 8 mm, preferably 4-6 mm. The ionization threshold and the therapeutic threshold are directly linked to the distance between two electrodes having different polarities. In this embodiment a pitch and/or clearance of at least 2 mm ensures that any arcing and potential scaring is avoided. The same applies with respect to the therapeutic threshold. A pitch and/or clearance of at most 8 mm, preferably between 4 and 6 mm, ensures that a continuous moat is achieved.

In one embodiment, the pitch and/or clearance, is chosen that it is greater than the central value between the ionization threshold and the therapeutic threshold. As the ablation portion may slightly be compressed during ablation, the pitch and/or clearance, chosen within the greater half of the region between the ionization threshold and the therapeutic threshold reliably ensures that the ablation area is of advantageous size regarding IRE even in a slightly compressed state.

In one embodiment, the diameters of two neighboring loop sections increase into the direction of the distal end of ablation portion forming a plunger type ablation catheter. The plunger type ablation catheter may be used for ablation in the ventricles or in the atrial area of the posterior left atrium. Alternatively, the diameters of two neighboring loop sections decrease into the direction of the distal end of the ablation portion forming a corkscrew type ablation catheter.

The corkscrew type ablation catheter may be used for ablation in the area of the atrial end of the PV. The diameters of loop sections may be, for example, between 10 mm and 40 mm. More specifically, if used in the left atrium, the widest loop section may have a diameter between 20-35 mm, preferably between 25-32 mm. The smallest diameter can be 12-22 mm, preferably 15-20 mm. The diameter is measured from both inner surfaces of opposite loop sections. For both areas, the form of the ablation portion is adapted to the specific form of the respective area to be ablated.

It is also within the scope of the present invention that the ablation portion may comprise a plurality of separate mapping electrodes, the mapping electrodes being configured for receiving electrical signals, e.g. electrical or biopotential, from vascular or atrial tissue. Alternatively, the electrodes used for ablation in the ablation mode may be used for mapping, namely receiving electrical biosignals, e.g. acquiring electrical or biopotential, from vascular or atrial tissue. During ablation these electrodes are in the ablation mode. This may enable mapping and ablation with a single ablation catheter for PVI as well as ablating some non-PV triggers for AF patients.

For example, in an embodiment, an additional loop section of the plurality of loop sections may exhibit a plurality of mapping electrodes. Additionally or alternatively, mapping electrodes may also be arranged—in addition to the ablation electrodes—on one or both of the two neighboring loop sections. A plurality of mapping electrodes may also be incorporated distal to the plurality of ablation electrodes, or medially within two ablation electrodes, e.g. between two ablation electrodes (along the respective loop section). Furthermore, the third loop section may comprise ablation electrodes in addition to or instead of the mapping electrodes.

As a suitable material, the ablation electrodes may comprise, for example, at least one of gold and a platinum/iridium alloy.

To achieve this without adding too many more ablation electrodes (which might render it more difficult to create contiguous lesions), relatively long ablation electrodes may be used. For example, a length of the ablation electrodes may be in the range 1-10 mm, preferably 3-5 mm. In one embodiment, the ablation electrodes may be sleeve-shaped or tubular. For example, a diameter of such a sleeve-shaped or tubular ablation electrode may be in the range of 2-2.5 mm. Further, as mentioned above, a length of the sleeve-shaped or tubular ablation electrode may be in the range of 1-10 mm, preferably 3-5 mm. Alternatively, a split electrode design may be used. In this embodiment two electrodes in form of half-shells separated by a gap are arranged at the inner side (facing the body lumen) and the outer side (facing the tissue) of the catheter. The gap may be 0.2-1 mm wide, preferably 0.5 mm wide. Such an embodiment is shown in FIG. 18c. Alternatively, electrodes may be solid but coated with insulating material on the inner side facing blood (the body lumen). Parylene, Polyimide or Teflon are examples of a suitable coating. The coating material should be an electrical insulator with high dielectric strength, in excess of 200 kV/mm.

In one embodiment, the ablation portion, and in particular the loop sections, may comprise a shape memory material. Preferably, the shape memory material is a super-elastic material (such as a super-elastic alloy), which is to say that the material is elastic and has a shape memory property. For example, Nitinol is a biocompatible super-elastic alloy that is suitable for the present purpose. In one variant, the ablation portion, and in particular the loop sections, may comprise an inner support element, such as an inner support wire, having a shape memory or super-elastic property. The shape memory support wire may have various stiffness and cross-sectional shapes in different sections. The inner support structure maintains the architecture and design integrity of the ablation portion and extends along at least a section of the ablation portion. The inner support structure may be realized as a Nitinol wire (for example a round, rectangular, square wire with variable cross section or tapered). In addition, this support structure comprises insulated with material, for example Parylene, Polyimide, Teflon at the outer surface of the wire. Further, the wire of the ablation portion may have sections with different diameter or cross-sectional shape in order to provide different stiffness.

In an embodiment, the ablation catheter may further comprise a steerable delivery sheath. Thus, in operation, a position of the ablation portion may be easily adjusted at the target visceral tissue until the contact of each ablation electrode is satisfied.

In one embodiment, the two neighboring electrodes of the plurality of electrodes of the ablation portion are staggered spaced along a distance greater than the ionization threshold. This means that electrodes may be positioned staggered as it spiraled within the axis of the loops. Accordingly, in one embodiment, the distance of the outer opposite surfaces of the loop section of each of the two neighboring loop sections in a direction perpendicular or inclined to the loop axis may be chosen greater than the ionization threshold, as well. As a result, if loops shift from side-to-side due to cardiac anatomy, the electrode are less likely to collide. Also, even if not colliding, electrodes are less likely to trigger arcing, as their relative spacing exceeds the ionization threshold.

In one embodiment, each of the electrodes are connected to an electronic control unit (ECU), wherein the connection is provided via a pulse generator to pair each two of at least two electrodes in a pre-defined manner. If there are more than two electrodes, for example 16 electrodes, e.g. each two electrodes which are accommodated adjacent along the loop sections may be paired (mode along the loop section) or each two electrodes which are accommodated adjacent across two neighboring loop sections (mode across loop sections) may be paired to be operated in a bipolar arrangement. Accordingly, 8 pairs may be formed from 16 electrodes in both modes. The pairing may be switched between the two modes. Further, the pairing may be switched to another pair of electrodes, for example along the loop sections. For pairing, the electrodes may be connected to a switch unit, wherein the switch unit is connected and controlled by the electronic control unit. The ECU may further be adapted to switch into the above mentioned ablation mode and mapping mode for each electrode, respectively. The switch unit realizes the pairing along the loop sections and, if applicable, the switching between the modes according to the control signals of the electronic control unit. The electronic control unit may comprise a microprocessor, computer or the like.

In one embodiment, the catheter shaft comprises at least two lumens separated by a material with a dielectric strength greater than a dielectric threshold suitable to withstand high-voltage PF pulses used with the above and below described catheter, for example with high-voltage PF pulses having an amplitude greater than 1 kV, greater than 2.5 kV or between 2.5 kV and 3.5 kV. Such material may be, for example, a polymer film, in particular a Polyimide film (e.g. Kapton® film) provided in form of tubing or a layer received by dipping. It has a dielectric strength of 160 kV/mm. The thickness of the polymer film (Polyimide layer) may be chosen in the range of 0.012 mm to 0.125 mm, for example. In this embodiment, the first lumen of the at least two lumens is configured to retain at least two electrode leads which are connected with electrodes providing the same first polarity and wherein the second lumen of the at last two lumens different from the first lumen is configured to retain at least two electrode leads which are connected with electrodes providing the same second polarity different from the first polarity. This embodiment allows to reduce the diameter of the catheter shaft as the isolation of each electrode lead is not necessary and to provide necessary safety with regard to flashover at the same time. If an electrode embodiment as shown in FIG. 18C is used, then the lumen structure is correspondingly adapted to accommodate an increased number of connecting wires. Same dielectric strength principles apply.

In one embodiment, the catheter shaft may have an overall length greater than 1 m from the handle to the distal tip of the ablation portion.

In one embodiment, at least two of the plurality of electrodes of the ablation portion are adapted to deliver high voltage monopolar PF energy or bipolar PF energy or a combination of monopolar and bipolar PF energy as described below. Some examples of applicable waveforms are shown in FIGS. 15A and 15B. Such waveforms, in combination with the loop structures described above, ensure one-shot application of electrical fields that are high enough to generate therapeutic effects capable of creating moats of conduction block, yet lower than ionization thresholds so to avoid arcing. The PFA pulses can be delivered gated by the QRS complex of the cardiac cycle. Alternatively, when ablation targets regions remote from ventricles, PFA pulses may be delivered asynchronously, without QRS gating. The electronic control unit is adapted to switch between monopolar PF energy and bipolar PF energy supply mode.

In another embodiment, the distal tip of the ablation portion is connected with steering wires or center wire which may be manipulated from a handle element provided at the proximal end of the catheter shaft. Accordingly, the center wire may be connected to an actuation mechanism within the handle element. Along the ablation portion, the center wire approximately run along a longitudinal axis of the catheter shaft. A steering plate, steering ring, or other known steering structures may be placed at the distal end of the catheter shaft, which connects to the distal spiral, or multiple loop, ablation section. The center wire connects to said steering structure. The center wire may be manipulated such that a longitudinal length of the ablation portion (i.e. its length along the longitudinal axis of the three-dimensional spiral/multiple loop structure) or the loop sections may be steered towards tissue targets, according to the therapeutic needs.

In one embodiment, the electrodes are distributed along the at least two loops in a way, that the angular separation between the most distal and the most proximal electrode is at least 360°. The angular separation is determined by the angle between the most distal electrode, the catheter axis and the most proximal electrode.

In one embodiment, the catheter comprises at least one irrigation lumen configured to apply an irrigation fluid at the treatment site. The at least one irrigation lumen may be connected to at least one individual irrigation opening at the ablation section. In an embodiment there may be individual irrigation openings at the individual electrodes, in between the electrodes or proximal and/or distal to the most proximal and most distal electrode at the ablation section.

The irrigation lumen may be connected to a source of an irrigation fluid at the proximal end of the catheter. The irrigation fluid may be a sterile fluid, preferably distilled water or a physiological saline solution having a low salinity, preferably of no more than 0.1%. Using distilled water or a saline solution with a low salinity reduces the salinity at the treatment site and therefor lowers the arcing risk further.

Another aspect of the present invention refers to an operation method of an ablation catheter for treatment of a patient's tissue, for example for a PVI procedure at a patient's heart tissue or vein tissue. Such method comprises operating an elongated catheter shaft and an ablation portion being arranged at a distal end of the catheter shaft. The ablation portion comprises a plurality of electrodes accommodated along the ablation portion. It also comprises at least two loop sections forming a three-dimensional spiral, The plurality of electrodes is energized with pulsed electric field energy which is delivered in a monopolar arrangement or in a bipolar arrangement or in a combination of a monopolar arrangement and a bipolar arrangement, and wherein the pulsed electric field energy is delivered in a charge-balanced manner.

The charge-balanced feature has potential benefits of minimizing bubbling (by lowering chances of electrolysis of the blood), arcing and skeletal muscle stimulation (direct or indirect via motor nerves).

Within the frame of this application, delivering pulsed electric field energy in a charge-balanced manner is understood as using pulses having a positive and negative pulse peaks and corresponding pulse widths charge-balance in a way, that the net charge delivered to the tissue as close to 0 µC as reasonably possible. One way to deliver charge-balanced pulsed electric field energy would be the use of biphasic pulses comprising a positive and a negative pulse section. The pulse width is the width of the positive section (or the negative section). Peak (amplitude) and width of the positive and negative section are designed to balance out each other. Consequently, the biphasic pulse itself is charge-balanced. Another way to deliver charge-balanced pulsed electric field energy would be the use several pulses of a pulse train, whereby the peak and the width of the individual pulses of the pulse train are designed to balance out each other.

In one embodiment, two neighboring electrodes along a loop section or two neighboring electrodes of different loop sections are energized with pulsed electric field energy in a bipolar arrangement. By doing so, electrical field vectors can be steered to generate a more complete moat of conduction block/electrical isolation.

In another embodiment, the voltage amplitude of the pulsed electric field is greater than 1 kV or greater than 2.5 kV or between 2.5 kV and 3.5 kV. Depending on the selected electrode configuration, the overall current amplitude may be within a range of 5-150 A.

In another embodiment, the pulse duration (pulse width of the positive or of the negative phase) is greater than 0.5 µs, preferably less than 30 µs. Preferably, the pulse is biphasic comprising a positive section comprising the positive pulse peak and a negative section comprising the negative pulse peak. The pulse width is the width of the positive section (or the negative section). Preferably, but not mandatory, the positive and negative phase complex would be charge balanced, so that the net charge delivered to tissue is as close to 0 µC as reasonably possible. Alternatively, the charge-balanced feature may be achieved over the duration of the pulse train. The net charge of the train would, in this case, be as close to 0 µC as reasonably possible. The charge-balanced feature has potential benefits of minimizing bubbling (by lowering chances of electrolysis of the blood), arcing (caused by ionization of the blood or of gases resulted from electrolysis) and skeletal muscle stimulation (direct or indirect via motor nerves). A biphasic pulse starting with a positive or negative section is understood as positive or negative (biphasic) pulse.

According to an embodiment, positive and negative pulses are separated by the interphase delay. The advantage of the pulse width according to the present invention is that the electric field acts sufficiently long against the cells so that pores are created by the electric field. The interphase delay may be chosen in the region 1 µs to 100 µs, so that the negative phase does not cancel too soon the effects of the positive phase and that the interphase delay is not too long. If the interphase delay becomes too long, the charge balance does not work. Negative and positive phases may be provided with the same amplitude or with a different amplitude, as long as a charge-balanced pulse train is/are achieved.

In an embodiment using biphasic pulses, the interphase delay is determined between two consecutive biphasic pulses, where a biphasic pulse is followed by an inverse biphasic pulse (for example a negative biphasic pulse following a positive biphasic pulse). The time between the first biphasic pulse and the start of the following inverse biphasic pulse is the interphase delay and as well within the range of 1 µs to 100 µs.

In a further embodiment, a pulse train (pulse sequence) comprising at least 1 pulse with a pulse width greater than 0.5 µs, preferably less than 30 µs is provided within a time period between 5-100 ms. The interpulse delay may be, for example, 0.1 to 100 ms. Preferably, the interpulse delay is longer than 1 ms. In one embodiment a pulse train of 10 pulses with an amplitude of 3 kV, a pulse width of 10 µs and 1 ms interpulse delay is used. In an alternative embodiment, a pulse train of 30 pulses with an amplitude of 1.625 kV, a pulse width of 15 µs and 5 ms interpulse delay is used. In a further embodiment, one pulse train or a plurality of such pulse trains, for example up to 500 pulse trains, are provided within a time period of at least 10 seconds, preferably within a time period of less than 2 minutes. Within this time, as pore recovery takes several seconds, the pores do not heal so that the cells program themselves to die thereby leading to IRE.

In one embodiment, a sterile irrigation fluid is applied at the treatment site whereby preferably distilled water or a physiological saline solution having a low salinity, preferably of no more than 0.1%, is used as irrigation fluid. Using distilled water or a saline solution with a low salinity reduces the salinity at the treatment site and therefor lowers the arcing risk further. The irrigation fluid may by applied via at least one individual irrigation opening at the ablation section. In an embodiment there may be individual irrigation openings at the individual electrodes, in between the electrodes or proximal and/or distal to the most proximal and most distal electrode at the ablation section.

Within the context of achieving charge balance, as described above, the pulse shape of a biphasic pulse may be, for example, a sine wave, a square wave, a triangle wave, exponential-decay or a sawtooth wave. Single pulses (positive or negative pulses) are preferably rectangular pulses.

Further, above described mapping electrodes may be used for the acquisition of electrical or biopotential from the surrounding vascular or atrial tissue. Mapping electrodes may have a similar structure compared with the ablation electrodes but may have dimensions slightly smaller than the ablation electrodes in order to provide a higher electrical signal resolution. Welding may be used to attach a conductor wire to one electrode. In one embodiment, smaller mapping electrodes (for example having a length of 1 mm) may be positioned between two ablation electrodes. The detected electrical voltage signals are transmitted via the respective electrode lead to the electronic control unit. Additionally or alternatively, the mapping electrodes may be used to acquire an electrical current. For example, mapping electrodes may be used to also measure local tissue impedance. This can be useful in order to monitor the degree of tissue contact or the progress of PFA effects. During the treatment of the patient, mapping may be conducted prior ablation and after one ablation step or after more than one ablation step in order to observe the ablation result and progress in ablation. In order to ease and improve assessment the received mapping signals of the mapping electrodes or electrodes operating in mapping mode, e.g. electrical potential signals, may be visualized using standard mapping or navigation technology. Thereby, the local conduction properties of the surrounding tissue may be mapped.

In one embodiment, the impedance is measured using the plurality of electrodes of the ablation portion of two neighboring loop sections in order to determine the relative distance between neighboring loop sections when they contact patient's tissue. In particular, the impedance is measured between two electrodes across neighboring loop sections. If the measured impedance is lower than a predefined impedance threshold, the neighboring loop sections are too close which should be avoided in order to prevent arcing if the electrodes of the neighboring section have different polarities. Further monopolar or bipolar impedance may be determined in order to prove uniform distribution of the electrodes and to thereby ascertain that the ablation portion is in contact with the patient's tissue along its entire outer surface.

In an embodiment, the impedance between two electrodes is measured over a certain frequency range, preferably an impedance curve depending on the frequency is determined. The frequency range could be between 10 kHz and 500 kHz. A flat impedance curve at low impedance values (for example 300 ohm at most) could indicate a contact, or collision, between the two electrodes. When two electrodes collide, or make electrical contact, the bipolar impedance phase increases, becoming significantly positive. This is because the inductance of the electrode wires will give the equivalent bipolar circuit (given the electrode collision) an inductive characteristic. A pronounced decay of the impedance curve at higher values (for example 100 ohm to 500 ohm) could indicate a good tissue contact between the two electrodes. A flat impedance curve in a medium impedance range could indicate poor tissue contact between the two electrodes. A flat impedance curve is to be understood as a dependence of the impedance from the frequency, where the impedance value measured at the high frequency deviates from the impedance value measured at the low frequency by less than 20%, preferably less than 10%. A pronounced impedance curve is to be understood as a dependence of the impedance from the frequency, where the impedance value measured the high frequency deviates from the impedance value measured at the lower frequency by more than 20%.

According to an aspect of the present invention, the operating method as disclosed above is used to operate an ablation catheter as disclosed above.

Another aspect of the present invention refers to a system to achieve a moat of cardiac conduction block in a tissue of a human or animal comprising:

1. a catheter comprising a catheter shaft and an ablation portion being arranged at a distal end of the catheter shaft with a plurality of electrodes accommodated along the ablation portion,
2. a high-voltage generator configured to deliver positive and negative high-voltage pulses comprising a pulse peak and a pulse width,
3. the catheter is adapted to be connected with the generator and to deliver the pulses to the plurality of electrodes accommodated along the ablation portion, and wherein
4. the generator is adapted to deliver pulsed electric field energy to the electrodes, whereby the pulse peak and pulse width are configured to generate pulsed electric field energy between the ionization threshold and the therapeutic threshold.

If the field intensity is sufficient to ionize the medium between electrodes, arcing could develop. Arcing presents increased levels of danger to patients, as it results in unintended tissue damage or barotrauma. Furthermore, the high temperatures of arcs may melt catheter materials, leaving foreign particles in the patient's blood stream. Therefore, it is important to configure the peak and pulse width in a way, that the resulting pulsed electric field energy at the electrodes is below the ionization threshold. One the other hand, the pulsed electric field energy needs to be sufficient enough to ensure one-shot application of electrical fields. Therefore pulse peak and pulse width are configured to generate pulsed electric field energy above the therapeutic threshold to generate therapeutic effects capable of creating moats of conduction block. Within the frame of this application (pulse) peak is understood as peak in voltage amplitude.

The system could comprise any catheter as described above.

The generator is configured to provide charge-balanced pulses having a positive and negative pulse peaks and corresponding pulse widths charge-balance in a way, that the net charge is zero. In an embodiment, biphasic pulses are generated which comprise a positive and a negative pulse section. The pulse width is the width of the positive section (or the negative section). Peak (amplitude) and width of the positive and negative section are designed to balance out each other. Consequently, the biphasic pulse itself is charge-balanced. The generator may be configured to generate biphasic pulses in the shape of a sine wave, a square wave, a triangle wave, exponential-decay or a sawtooth wave.

Another way to way to deliver charge-balanced pulsed electric field energy would be the use several pulses of a pulse train, whereby the peak and the width of the individual pulses of the pulse train are designed to balance out each other.

The generator could be configured to deliver pulses having a pulse width between 0.5 µs and 30 µs. Individual pulses could be separated by an interpulse delay between 0.1 ms and 100 ms. The interphase delay may be within the range of 1 µs to 100 µs.

The generator could be also configured to generate pulse trains comprising at least one pulse, preferably at least two pulses. A pulse train could comprise biphasic pulses and/or monophasic pulses. The length of such a pulse train could be between 5 ms and 100 ms. The generator may be configured to deliver up to 500 pulse trains in a time frame of at least 1 second. Preferably the pulse trains are delivered less than 2 minutes.

The system could further comprise an apparatus to measure an electrocardiogram and detect the characteristic peaks of the QRS cycle, the P-wave and/or T-wave. The apparatus to measure an electrocardiogram is configured to be connected with and/or to communicate with the generator. The apparatus to measure an electrocardiogram is configured to provide a trigger signal corresponding to the detection of at least one of the following: the QRS cycle, the P-wave and/or T-wave. The generator is configured to start at least one pulse or a pulse train in connection with the trigger signal.

In an alternative embodiment, the measured electrocardiogram is analysed by the generator and at least one pulse or a pulse train are started in connection with the QRS cycle, the P-wave and/or T-wave.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein schematically and exemplarily.

FIG. 16A shows the QRS detector signal (top trace), the PFA trigger signal (middle trace) and the ECG (bottom trace) over several heart beats. FIG. 16B shows a detail into one heartbeat. The PFA trigger signal (middle trace) falls within the refractory period of the cardiac cycle. FIG. 16C shows the PFA pulse artifact, as recorded during a preclinical study;

FIG. 18A shows the catheter of this invention facing a PV. FIG. 18B shows the catheter of this invention deployed when pressed against PV wall. Note the clearance between spiral arms. FIG. 18C shows an alternative split-tip electrode construction;

FIGS. 20A-B show two examples of measured impedance over frequency.

DETAILED DESCRIPTION

FIGS. 1, 3, 4 and 12 schematically and exemplarily illustrate a distal portion of an ablation catheter 1 in accordance with a first embodiment. The ablation catheter may be used for PFA, when used with the PFA generator and accessories, and is indicated for use in cardiac electrophysiological mapping (stimulation and recording) and in high-voltage, pulsed-field cardiac ablation. Peak voltages are, for example, without limitation, +/−1 kV to 3 kV with a pulse width of up to 30 µs. Higher peak voltages (e.g. up to 10 kV) may be used provided the pulse duration is correspondingly shorter (e.g. 0.5 µs). The catheter 1 has an elongated circular catheter shaft 10, which may connect with a handle comprising a steering mechanism at a proximal end (not illustrated). As a result, the catheter may control deflections of the depicted distal section carrying the ablation electrodes.

Figure 1:
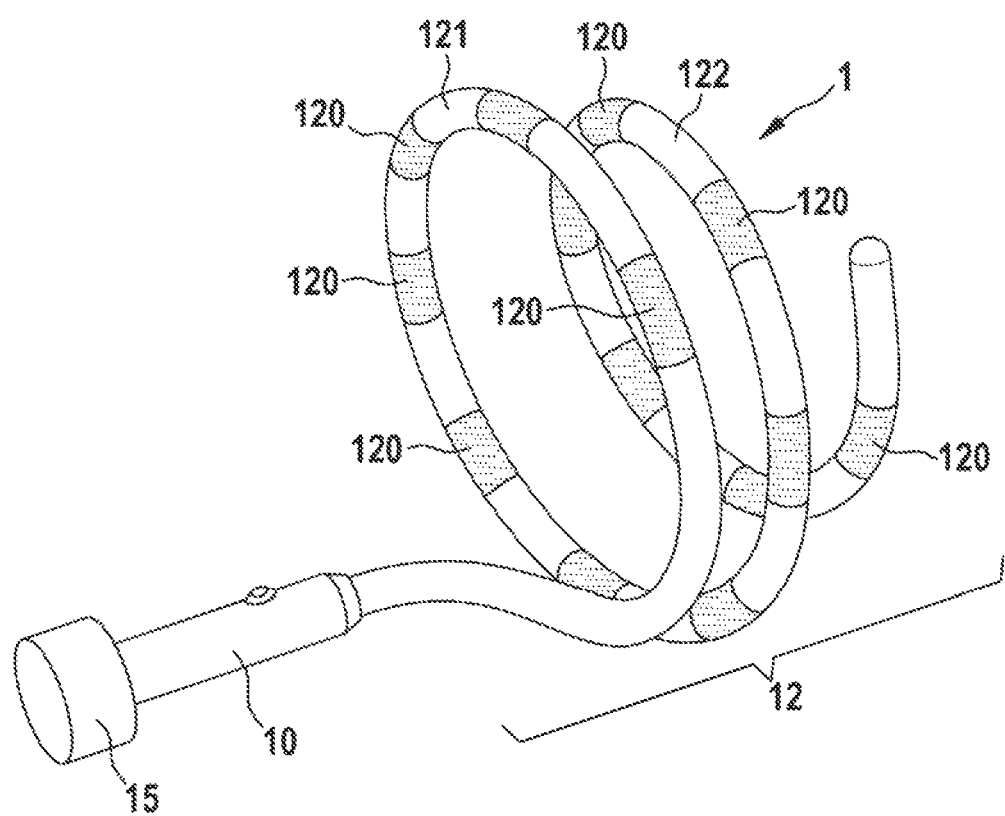
FIG. 1 depicts a distal end of a first embodiment of an ablation catheter in a perspective side view.

At the illustrated distal end of the catheter shaft 10 an ablation portion 12 is arranged, which comprises a plurality of loop sections 121, 122. The concept of loop sections includes embodiments that use continuous loops or spirals configurations. The catheter shaft may have an effective length of approximately 115 cm from the distal tip of the ablation portion 12. Each of a first loop section 121 and a neighboring second loop section 122 exhibits ablation electrodes 120 (altogether, for example, 14 electrodes), which are configured for delivering energy to tissue. Although two loops are illustrated in FIG. 1, more can be used. It is preferred that at least a partial third loop is used in order to provide sufficient overlap among resulting ablation zones. Said overlap would increase chances of achieving a conduction block moat without drops in lesion continuity, contiguity or transmurality. As an example, see catheter illustration in FIG. 14. The distal section comprises at least 45° of overlap of a $3^{rd}$ loop section with the previous two sections. In particular, the ablation catheter 1 may be configured for delivering an electrical high voltage PFA signal to tissue via the ablation electrodes 120. For example, the ablation electrodes 120 may consist of or comprise gold and/or a platinum/iridium alloy. Alternatively, electrodes 120 from different loop sections may be positioned so that electrodes of same polarity are aligned. Either the staggering or the polarity-based approach ensures that electrodes of opposite polarities would not collide when the spiral catheter is compressed.

In the exemplary embodiment illustrated in FIG. 1, the ablation electrodes 120 of the second loop section 122 are arranged partly in a staggered manner with respect to the ablation electrodes 120 of the first loop section 121.

The loop sections 121, 122 may further exhibit a plurality of mapping electrodes, which are configured for receiving electrical signals from tissue.

Figure 5:
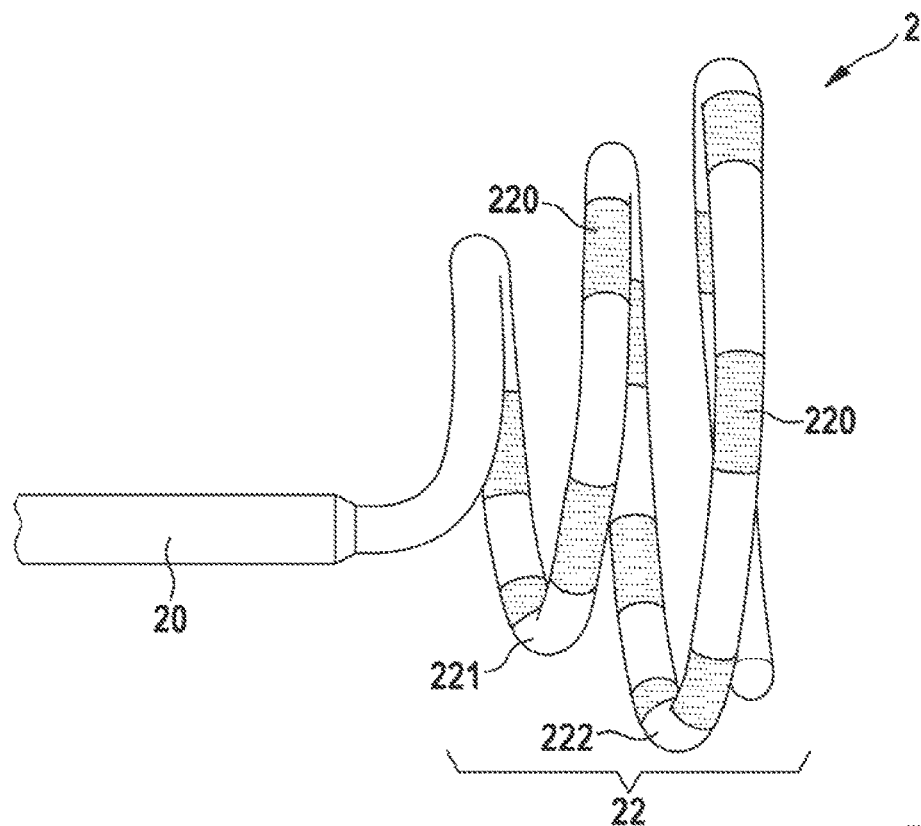
FIGS. 5 to 7 depict a distal end of a second embodiment of an ablation catheter in a side view, a front view and in a perspective front view.
Figure 6:
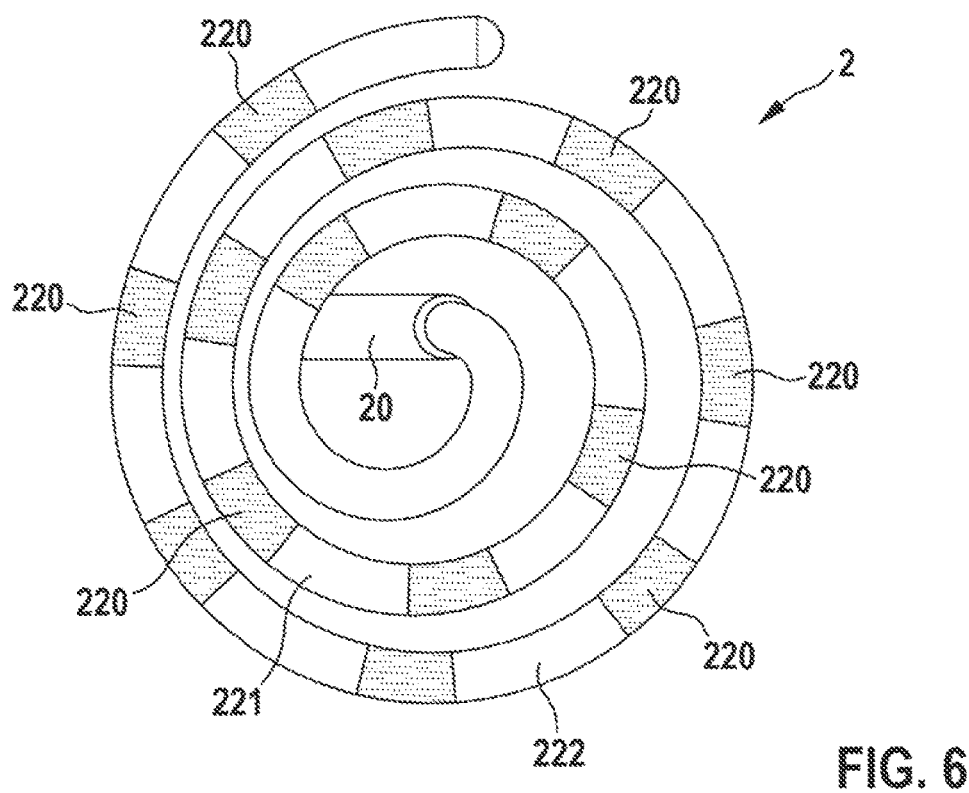
Figure 7:
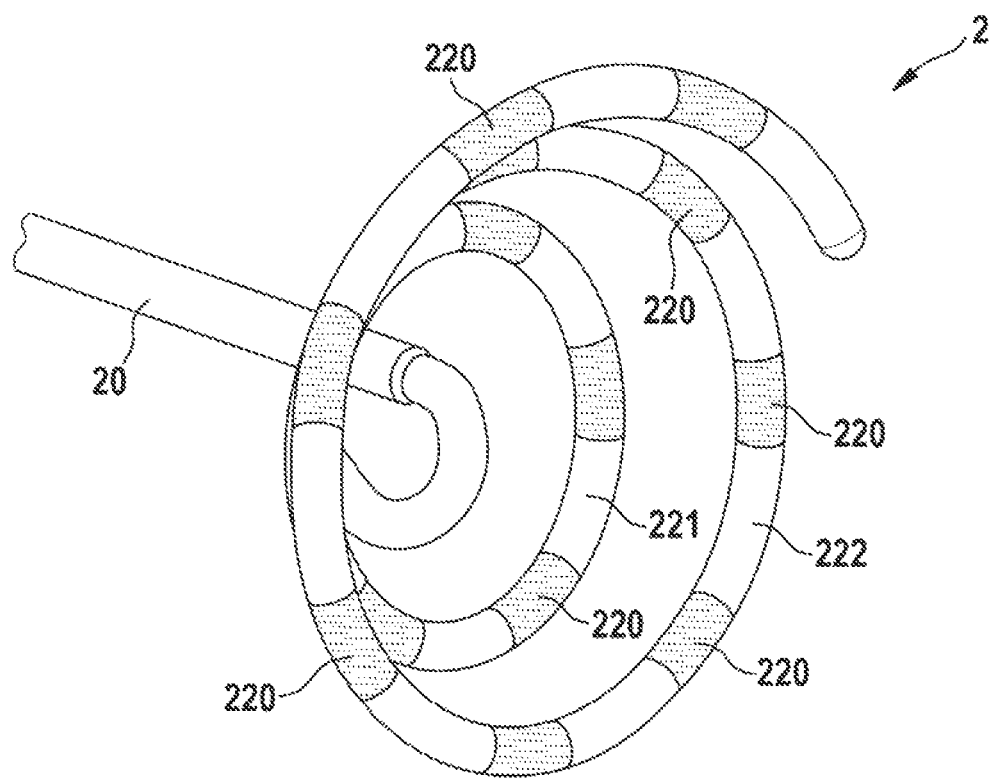

Together, the loop sections 121, 122 form a three-dimensional spiral, which form a corkscrew-similar form. Alternatively, they may form a plunger-like configuration, as shown in FIGS. 5-7. It should be noted that respective diameters of the loop sections 121, 122 are such that the first, more proximal loop section 121 has a greater inner diameter D1 (for example 30 mm, see FIG. 12) than the second, more distal loop section 122 (inner diameter D2, for example 24 mm). At the furthest distal tip of the ablation portion 12 the inner diameter D3 is even lower (for example 18 mm). In general, the diameters of loop sections may be, for example, between 10 mm and 40 mm. More specifically, if used in the left atrium, the widest loop section may have a diameter between 20-35 mm, preferably between 25-32 mm. The smallest diameter can be 12-22 mm, preferably 15-20 mm.

The loop sections 121, 122 may comprise a shape memory material, for example, in the form of an inner structural support wire (not illustrated), for example a Nitinol wire as described above. In particular, the loop sections 121, 122 may have super-elastic properties.

The ablation portion 12 may be constrained into an essentially elongate shape for the purpose of delivery to a target region in the human body by means of a (fixed or steerable) delivery sheath 15, which may also be referred to as an introducer sheath. At the target position, upon exiting a distal end of the delivery sheath 15, the ablation portion 12 may then recoil to its original (biased) shape.

The length of each electrode 120 along the respective loop section 121, 122 is, for example, 4 mm. In general, the electrode length is in the range 1-10 mm, preferably 3-5 mm. The catheter shaft 10 size may be compatible with an 8.5 F ID sheath and may consist of radiopaque extrudable polymer and, if applicable, a polymer-reinforcing braid. In general, the size of the catheter shaft 10 may be compatible with a 7 F to 14 F ID sheath. The width between neighboring electrodes along the respective loop section may be chosen between 1 mm and 10 mm, preferably 3-6 mm, in order to provide a contiguous ablated area at the patient's tissue.

Figure 2:
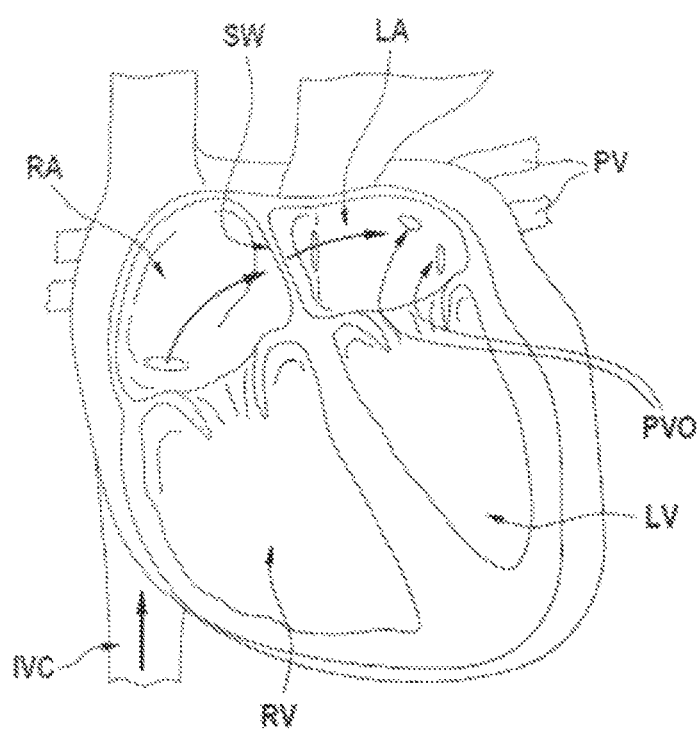
FIG. 2 illustrates a delivery path for an ablation catheter leading to a pulmonary vein ostium of a human heart.
Figure 3:
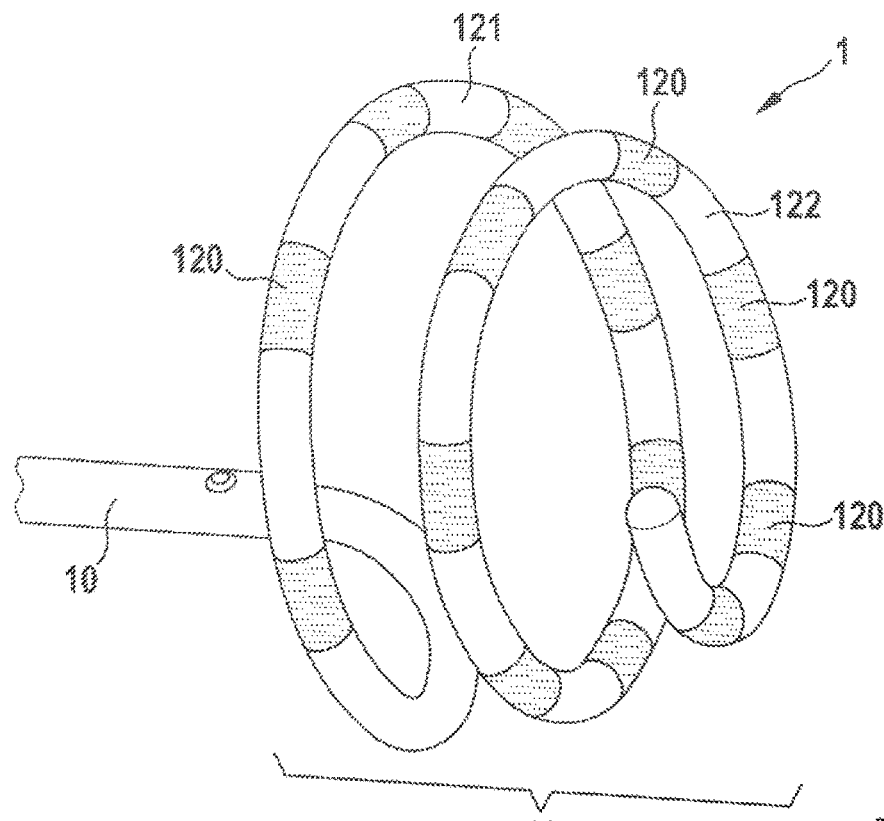
FIGS. 3 and 4 show the distal end of the embodiment of FIG. 1 in a perspective front view and in a side view.
Figure 4:
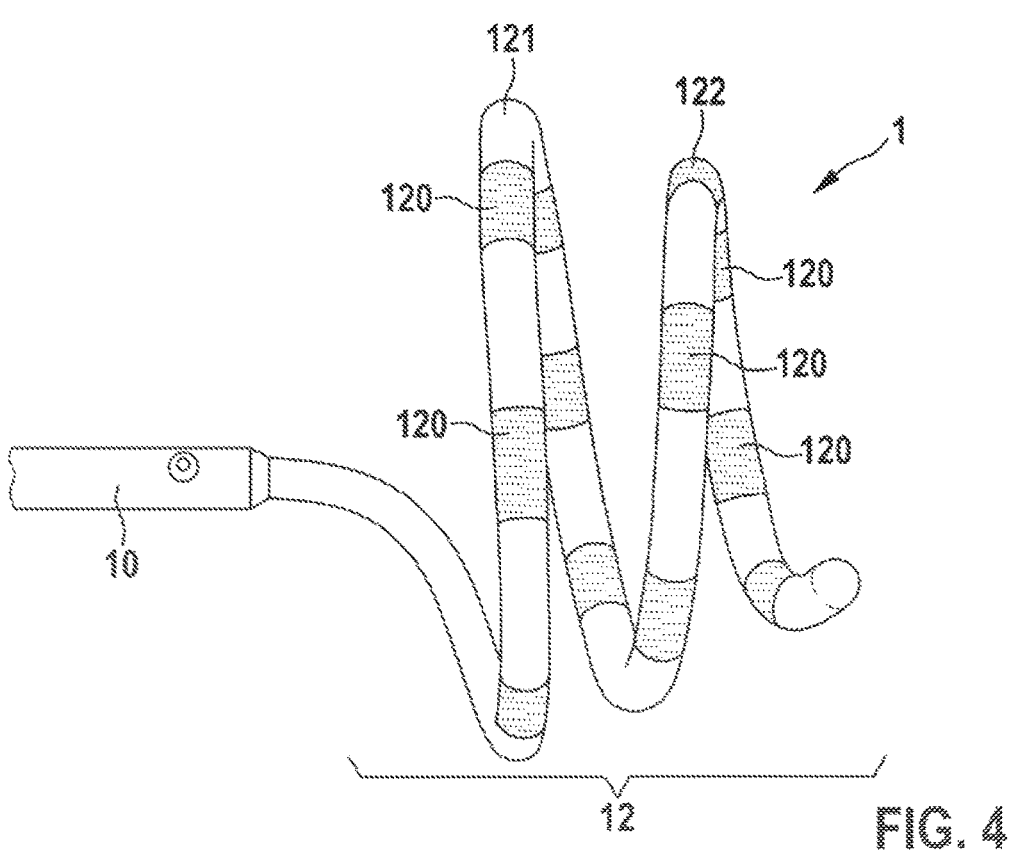

FIG. 2 schematically and exemplarily illustrates a delivery path for an ablation catheter 1 leading to a pulmonary vein ostium (PVO) of a human heart. For orientation, the inferior vena cava (IVC), the right atrium (RA), the right ventricle (RV), the left atrium (LA), the left ventricle (LV), as well as pulmonary veins (PV), each with a PVO, are shown. The large black arrows indicate a delivery path passing through the IVC, the RA, transseptally through the septal wall (SW), and into the LA. Finally, using appropriate deflection means, catheter 1 is steered to PVO regions. There, the corkscrew type ablation catheter may be used for ablation in the area of the atrial end of the pulmonary vein close to PVO. The form of the ablation portion 12 is configured such that it fits to the dimensions of the targeted PVO. Alternatively, corkscrew-type catheters may be used to ablate at the SVC or at Appendages, such as the left or right atrial appendages (LAA or RAA).

The second embodiment of an ablation catheter 2 shown in FIGS. 5 to 7 is adapted to the use for ablation in the atrial area of the left atrium LA surrounding the PVOs, or located between PVOs (e.g. posterior LA wall). Alternatively, catheter 2 may be well suited for ablations on ventricular (RV or LV) walls, or in the RA (e.g. free RA wall, Tricuspid Valve annulus, etc.). The ablation portion 22 comprises two loop sections 221 and 222 with a plurality of ablation electrodes 220 (and, if applicable also with mapping electrodes) analogous to the first embodiment. However, the ablation portion 22 is formed like a three-dimensional spiral having the form of a plunger, where the more proximal first loop section 221 has a lower diameter than the second, more distal loop section 222.

Figure 8:
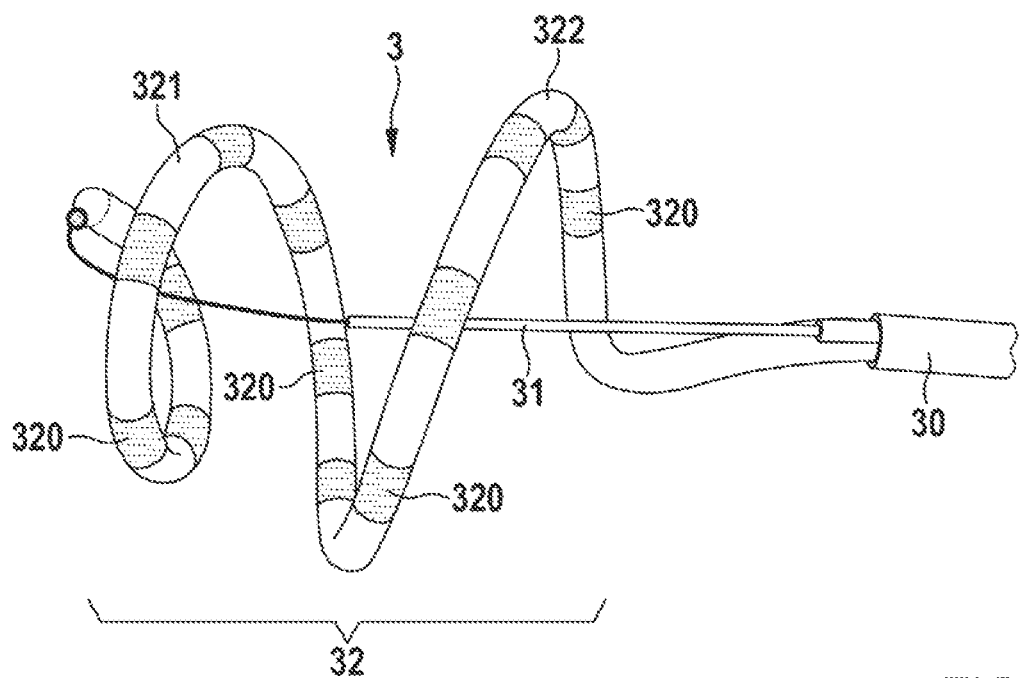
FIGS. 8 to 11 depict a distal end of a third embodiment of an ablation catheter in a side views and a front view.
Figure 9:
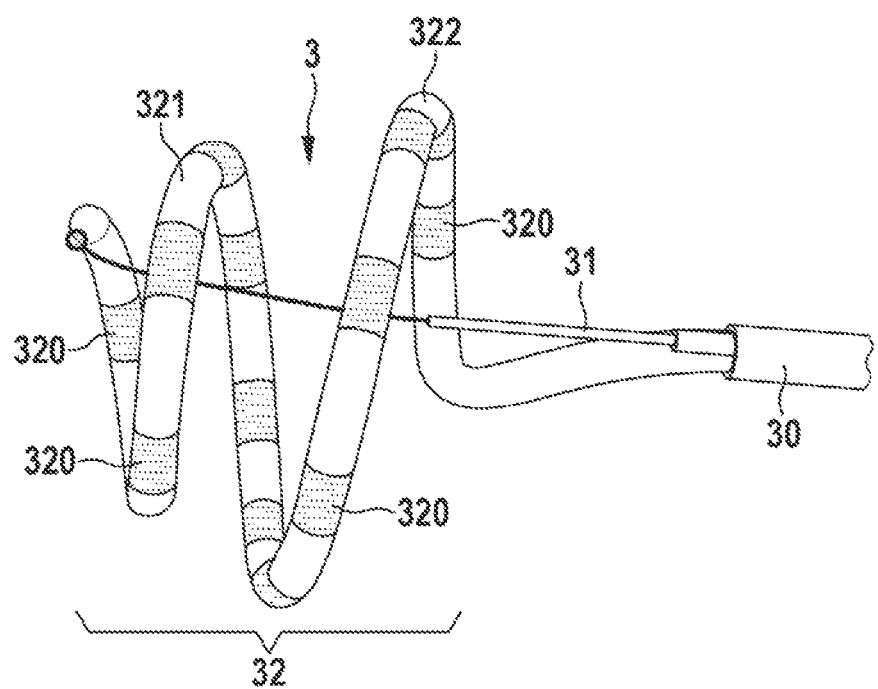
Figure 10:
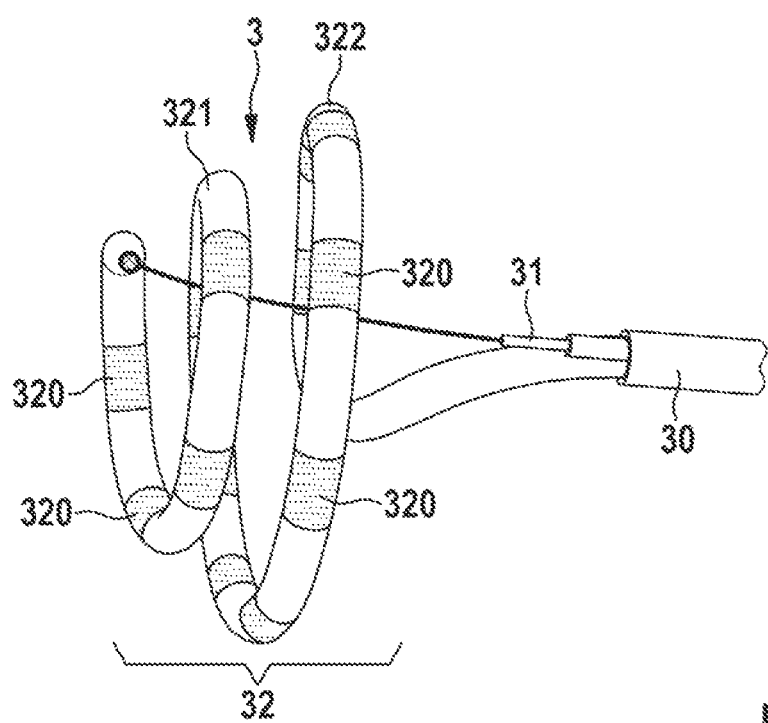
Figure 11:
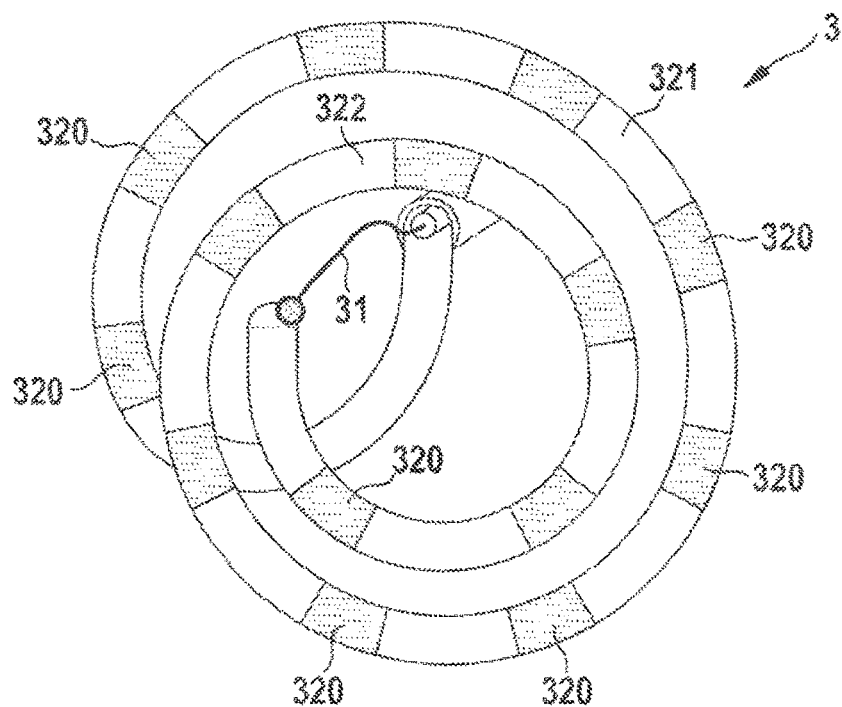
Figure 12:
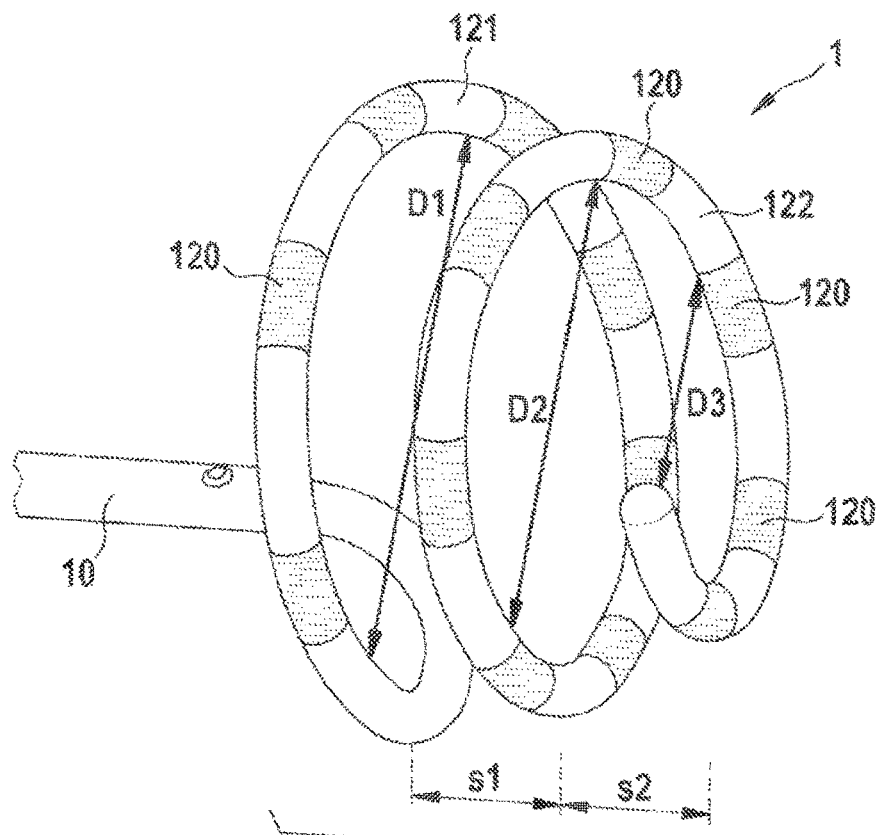
FIG. 12 shows the distal end of the embodiment of FIG. 1 in a perspective side view with some marked dimensions.

There is a third embodiment shown in FIGS. 8 to 11 similar to the first embodiment. Without limitations though, elements of this embodiment (e.g. center wire 31, for spiral expandability or compression) may be used with other type of spiral catheter. Additional to the construction of the first embodiment the third embodiment of an ablation catheter 3 comprises a center wire 31, used to facilitate expandability or compression of the distal section. Center wire 31 is connected with the distal tip of the ablation portion 32. Ablation portion 32 carries ablation electrodes 320. Center wire 31 is running approximately along the longitudinal axis of the spiral formed by the ablation portion and its two loop sections 321, 322. Center wire 31 enters and runs inside catheter shaft 30. At the proximal end of the catheter, center wire 31 connects with actuating element associated with or integrated in the catheter handle. The center wire 31 may be manipulated such that a longitudinal length of the ablation portion 32 (i.e. its length along the longitudinal axis of the three-dimensional spiral of the ablation portion 32) and, accordingly the diameters of the loop sections 321, 322 may be changed and adapted to the therapeutic needs and the local situation. In the drawing of FIG. 8 the longitudinal length of the ablation portion is greatest compared with the drawings of FIGS. 9 and 10 because the center wire pushes the distal tip of the ablation portion 32 in distal direction. Accordingly, the diameter of the loop sections 321, 322 is smallest. FIG. 10 shows the shortest longitudinal length of the ablation portion 32 of the ablation catheter 3. This is achieved by pulling the center wire 31. The ablation catheter 3 shown in FIG. 9 has a nominal longitudinal length of the ablation portion 32, which is between those of FIGS. 8 and 10. Hence, the diameter of the loop sections 321, 322 is greatest in FIG. 10 and smallest in FIG. 8.

Reliable full ablation along a whole circumference is achieved with the first and the second embodiment at their respective position within the heart or the vein to which the form is adapted. A small compression of the ablation portion 12, 22 of the respective catheter 1, 2 may be possible during ablation into the direction of the longitudinal axis of the spiral, but the distance of the loop sections 121, 122 or 221, 222 is still in the region limited by the therapeutic threshold and the ionization threshold.

In order to cause IRE, spare adjacent tissue and shorten ablation time, the pitch of neighboring loop sections is chosen between the ionization threshold and the therapeutic threshold as explained in detail above. Referring to the first embodiment shown in FIG. 12, the first pitch, or clearance, s1 of the first loop section 121 and the second loop section 122 is approximately 5 mm and the second pitch, or clearance, s2 of the second loop section 122 and the furthest distal end of the ablation portion 12 is approximately 5 mm, as well. In general, the pitch, or clearance, should be between the ionization (2 mm) and therapeutic thresholds (up to 8 mm). As presented above, it is important that the angular offset between most distal and most proximal electrodes on any of the catheters #1, #2 or #3, exceeds 2*360°, preferably it is 2*360°+45° (i.e. two full loops plus ⅛th of a third loop).

The ablation procedure using one of the ablation catheters 1, 2, 3 may start after the ablation portion 12, 22, or 32 is in the correct position relative to the targeted tissue, for example at a PVO. The ablation electrodes 120, 220, 320 will provide pulsed electric RF field in a monopolar or bipolar arrangement. Peak voltages are, for example, without limitation, +/−1 kV to 3 kV with a pulse width of up to 30 μs. Higher peak voltages (e.g. up to 10 kV) may be used provided the pulse duration is correspondingly shorter (e.g. 0.5 μs). The pulse width may be 12 μs (between 0.5-30 μs) forming a pulse train comprising up to 500 pulses/train. Any of the waveforms illustrated in FIG. 15 may be used.

Figure 15A:
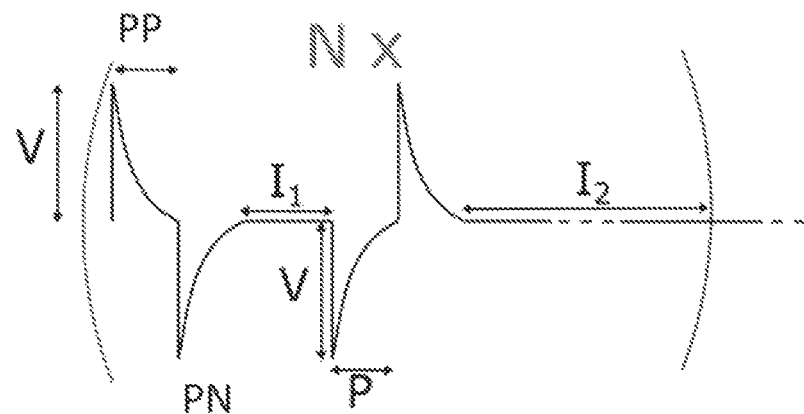
FIGS. 15A-B illustrate exemplary waveforms that are charge balanced. Waveform in FIG. 15A is of exponential decay type. Waveform in FIG. 15B is of rectangular type.

Without limitations, as an example, waveform in FIG. 15A shows biphasic exponentially decaying voltage pulses suitable for PFA treatment. Over the entire waveform complex, the exponential decays achieve a charge-balanced goal, needed to minimize chances of bubbling, arcing or undesired tissue stimulation. Such waveforms may be achieved by using high-voltage output stages which are AC-coupled to the ablation electrodes 120, 220 or 320. The two biphasic pulses shown in FIG. 15A form a pulse train, which could be repeated N-times. The biphasic pulses consist of a positive section PP and a negative section PN. As shown in FIG. 15A a positive biphasic pulse is followed by an inverse negative biphasic pulse. The interphase delay $I_1$ is the time between the end of the negative section PN of the first biphasic pulse and the start of the positive section of the following pulse. As defined above the pulse width P corresponds to the length of the positive/negative section PP/PN, if biphasic pulses are used. The next pulse train starts after the interpulse delay $I_2$.

Figure 15B:
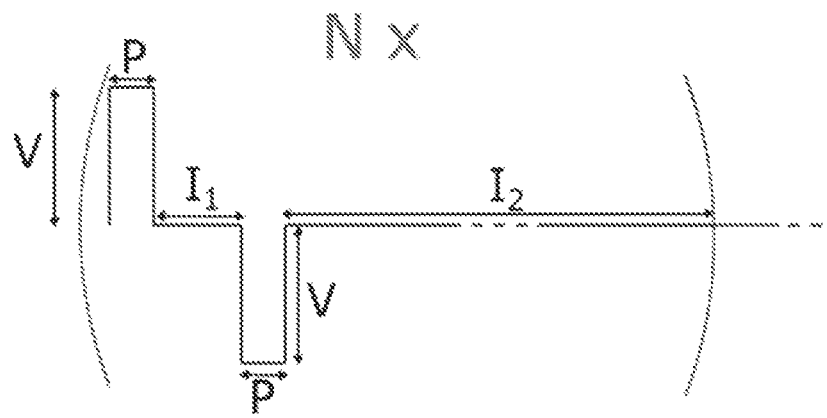

Similarly, FIG. 15B shows an example of suitable PFA waveforms which have rectangular shapes. The rectangular pulses as shown in FIG. 15B are characterized by the voltage peak V and the pulse width P. A positive rectangular pulse is followed by a negative rectangular pulse after the interphase delay $I_1$. The two pulses shown in FIG. 15B form a pulse train, which is repeated N-times. The next pulse train starts after the interpulse delay $I_2$. These waveforms are also charge balanced. Such charge-balanced rectangular waveforms may be achieved by using DC-coupled high-voltage output stages with reasonably accurate control of the positive and negative phase amplitude and duration. As a result, the net charge (current amplitude*pulse width) can be controlled to achieve net balancing.

Figure 16A:
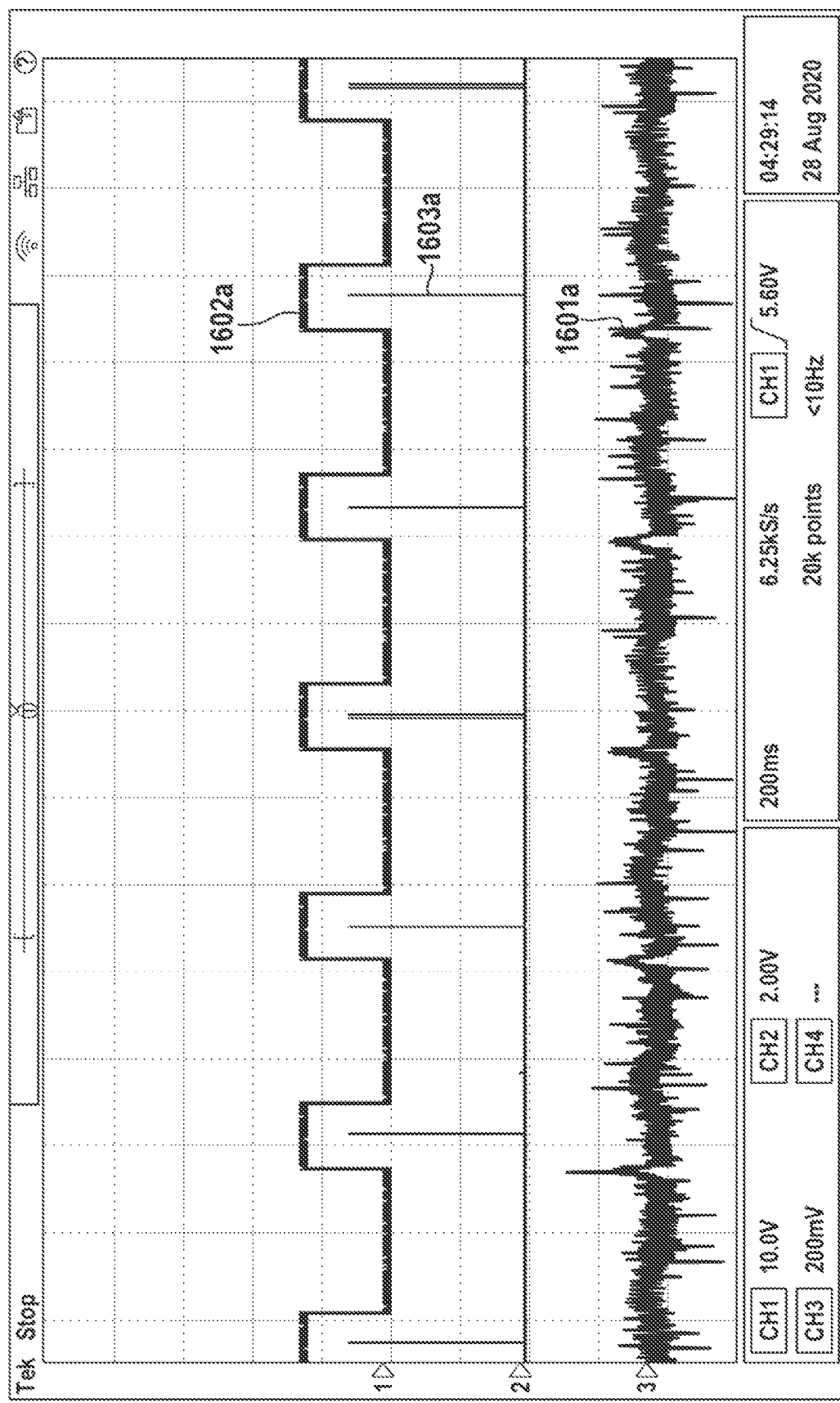
FIGS. 16A-C illustrate the concept of QRS gating.
Figure 16B:
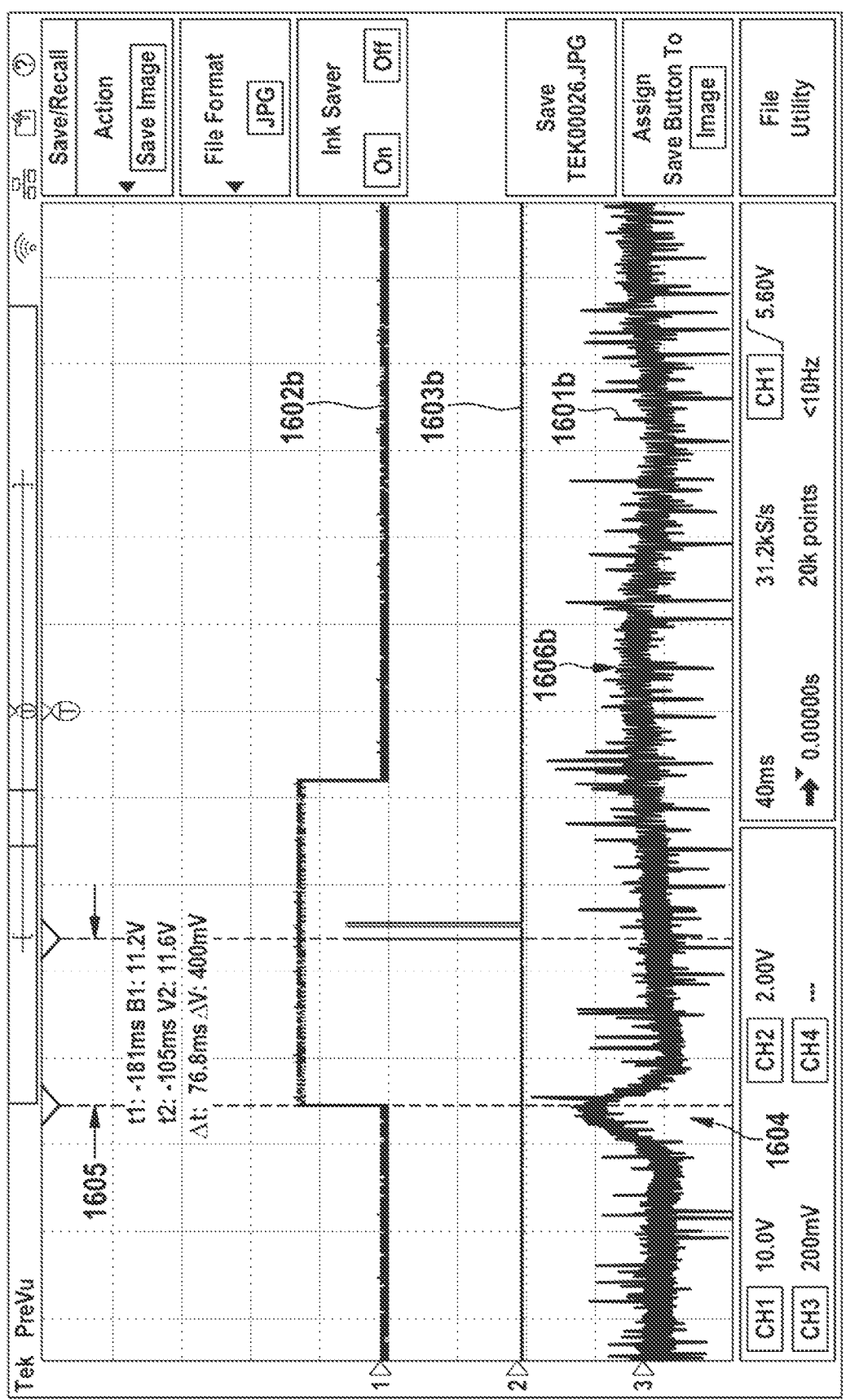
Figure 16C:
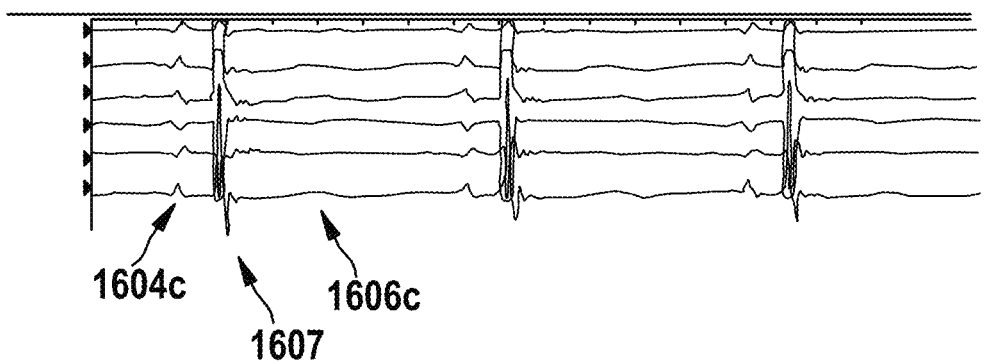

FIGS. 16A-C show QRS-gated output waveforms. A typical lead-I ECG waveform 1601a is shown in FIG. 16A. The output of the QRS detector is illustrated as signal 1602A. The trigger of the PFA waveform is shown as signal 1603a. FIG. 16B provides a zoomed-in view of FIG. 16A. The ECG waveform 1601b is represented over one cardiac cycle. Its R-wave 1604 is detected by the QRS detector output 1602b. After a programmed delay 1605, the PFA waveform trigger 1603b is turned on. In this embodiment, delay 1605 is shown to be about 70 ms. Delay 1605 may be between 20-150 ms, depending on the heart rate. It is important to make sure PFA pulses are applied within the refractory period of the heart. As FIG. 16B shows, in this particular example the train of pulse ends before the beginning of T wave 1606. FIG. 16C shows an example of PFA pulses artifacts, as recorded with a standard cardiac recording system. R wave 1604c is seen being followed by artifacts 1607 caused by delivery of PFA pulses. Artifacts 1607 safely end before the beginning of T waves 1606c. The process described above delivers one train of pulses within one cardiac cycle. In the above example, 10 pulses/train were delivered using waveform 1501 from FIG. 15A. Persons of skill in the art may modify the above approach by using other known parameters without departing from the essence of this invention. For example up to 500 pulse trains may be provided. However, although not required, it is preferable to select a number of trains so that to keep the PFA application time to greater than 1 s (to allow of cell membrane poration) but less than 2 min (to avoid long procedures). The interphase delay may be 1-100 μs. The interpulse delay may be 0.1 ms or 100 ms.

Figure 13:
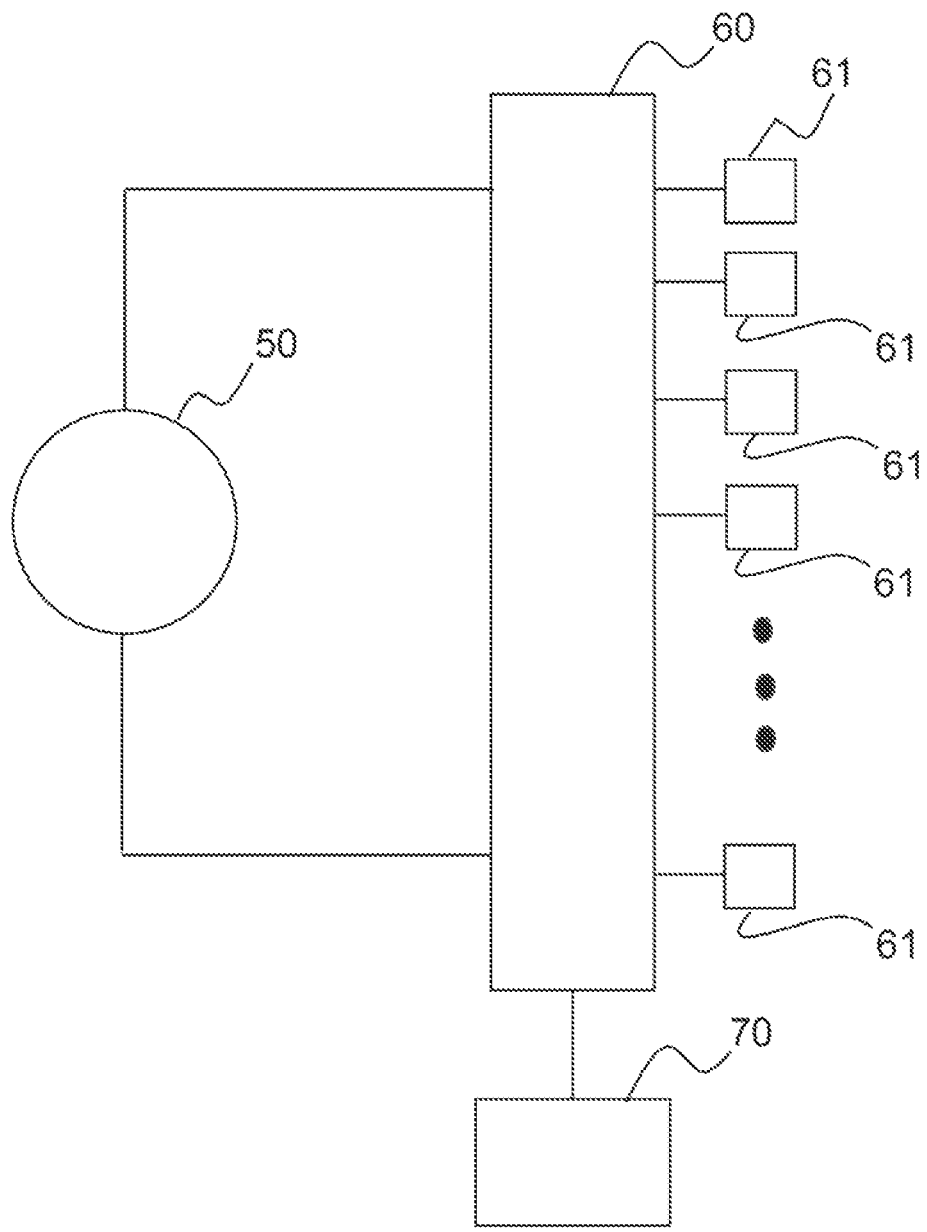
FIG. 13 shows part of the electric control of the electrode leads for the embodiment of FIG. 1.
Figure 14:
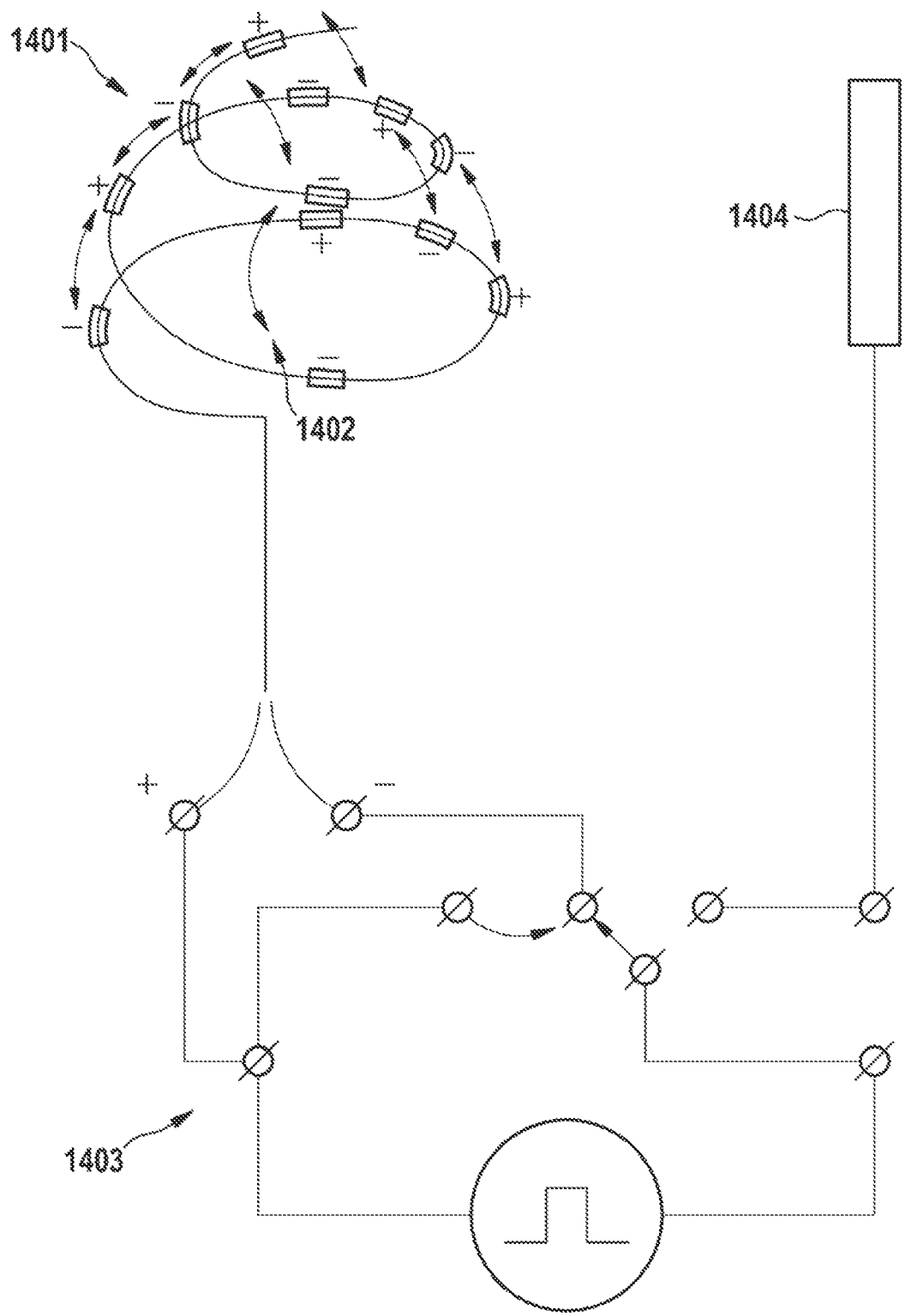
FIG. 14 shows electrical field vector distribution electronically steered to achieve a moat of conduction bloc.

The electric field generation (in particular voltage, current and impedance) is monitored by an electronic control unit (ECU) 70 which is connected to the leads 61 of the electrodes 120, 220, 320 and produced by a waveform generator 50 (see FIG. 13). FIG. 14 also shows connectivity that can be used to generate monopolar or bipolar electric fields. ECUs in FIGS. 13 and 14 may control application of PFA fields with a goal of achieving wide coverage of the tissue space in between catheter loops or spirals. FIG. 14 illustrates a catheter 1401 (such was #1, #2 or #3 from FIGS. 1-10) with its electrodes driven by ECU 1403. ECU 1403 can be controlled to deliver field vectors 1402 that cover the tissue zone in between catheter 1401 spiral arms/loops. By doing so, a moat of conduction block/electrical isolation is more likely to be achieved.

In the bipolar arrangement neighboring (adjacent) electrodes 120, 220, 320 may be paired along the loop sections 121, 122, 212, 222, 321, 322 or across two neighboring loop sections 121 and 122; 221 and 222; 321 and 322. Further, the electrodes 120, 220, 320 may be used in monopolar arrangement. In this case, a ground pad 1404 may be provided at the surface of the patient's body. Alternatively, reference electrodes associated with the catheter shaft may be used.

In order to switch between different bipolar arrangements or between monopolar and bipolar arrangement, the ablation catheter 1, 2, 3 may comprise a switch unit 60 connected to and controlled by the ECU 70. The switch unit 60 provides the respective phase of the pulsed electric field provided by the waveform generator 50 to the predefined electrode lead 61 and thereby to the predefined electrode 120, 220, 320, wherein each electrode lead 61 is electrically connected to one particular electrode 120, 220, 320 at the ablation portion 12, 22, 32. The switch unit 60 comprises a switch matrix and may realize any configuration of phase distribution, for example, such that two neighboring electrodes along the loop sections or across the loop sections are paired to achieve the aforementioned uniform moat of conduction block. Any other configuration is possible. The switching signal and configuration information is provided by the ECU 70. ECU 70 further may provide data processing of electrical or biopotential data or impedance data acquired by mapping electrodes of ablation catheters 1, 2, 3. As indicated above mapping electrodes located in the ablation portions 12, 22, 32 may comprise mapping electrodes for determining the electrical potential of the surrounding tissue in order to observe the ablation progress at pre-defined time points during ablation procedure. Alternatively, the ablation electrodes 120, 220, 320 may be switched into the mapping mode and back into the ablation mode. Further, the impedance between neighboring electrodes or across two different, neighboring loop segments may be determined prior to delivery of PFA energy. Thereby impedance (monopolar or bipolar) is monitored whether the neighboring loop segments and hence the electrodes of these segments are located in a sufficient distance to the other loop segment or electrode, respectively. By monitoring impedance, ECU 70 or 1403 may alert the user when any two electrodes are too close, with respective inter electrode distance falling below the ionization threshold. Conversely, users may be alerted when impedance measurements indicate that the inter electrode distance exceeds the therapeutic threshold.

As indicated above, the catheter shaft 10, 20, 30 may comprise two lumens separated by a material, e.g. Kapton®, with a dielectric strength greater than a dielectric threshold for high-voltage PFA pulses. The first lumen may retain, for example, 7 electrode leads 61 providing the first polarity and the second lumen may retain, for example, 7 electrode leads 61 providing a second polarity thereby reducing the overall diameter of the catheter shaft.

Figure 17:
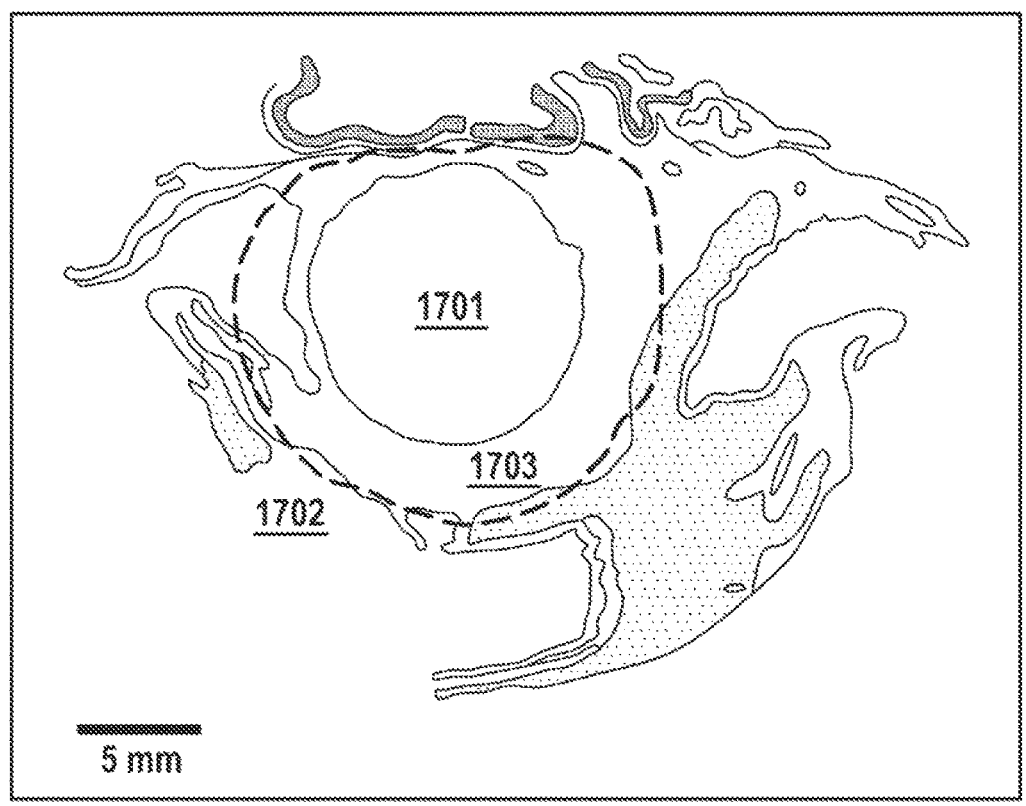
FIG. 17 shows an actual histology slide identifying the moat of conduction block (or electrical isolation) around the right superior pulmonary vein (RSPV)
Figure 18A:
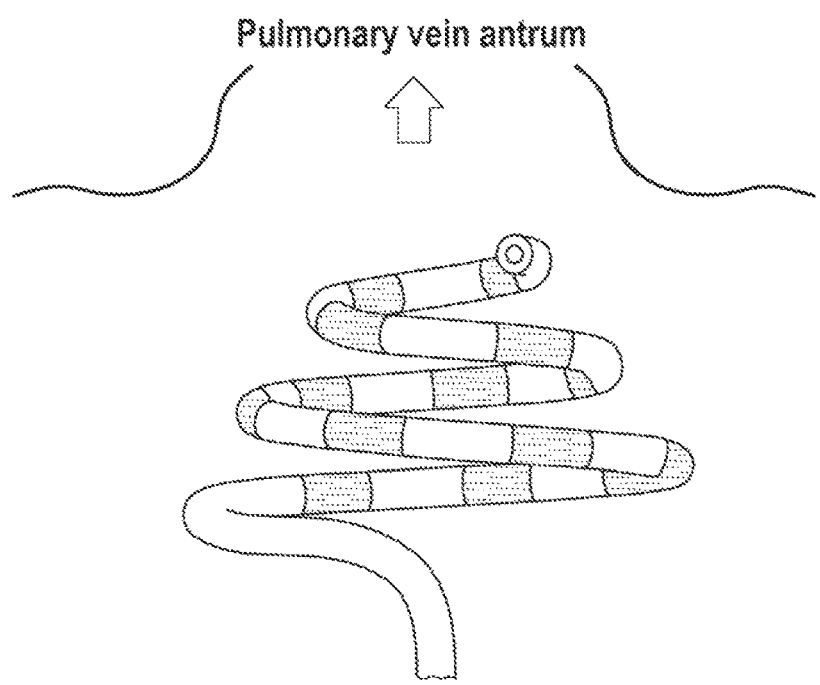
FIGS. 18A-C further exemplify a possible electrode distribution on a spiral distal section.
Figure 18B:
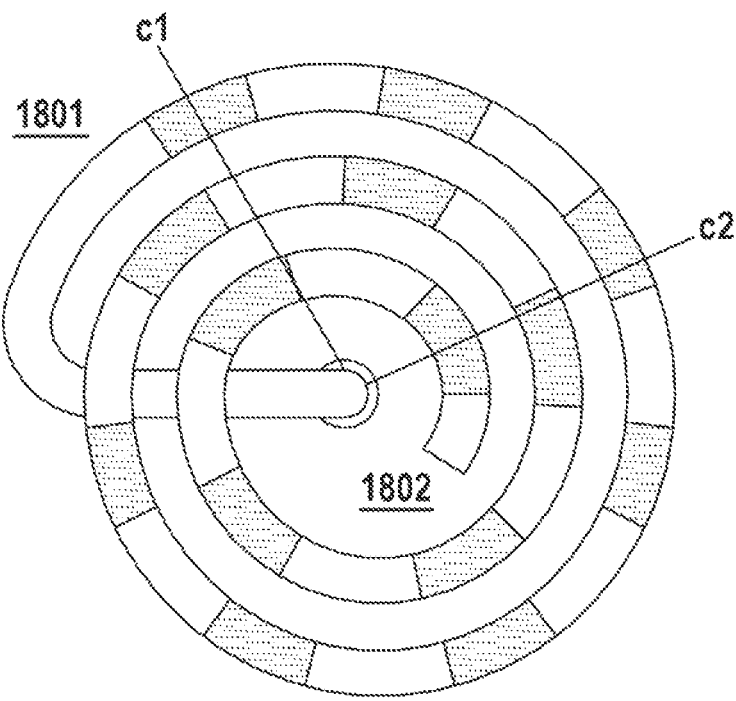
Figure 18C:
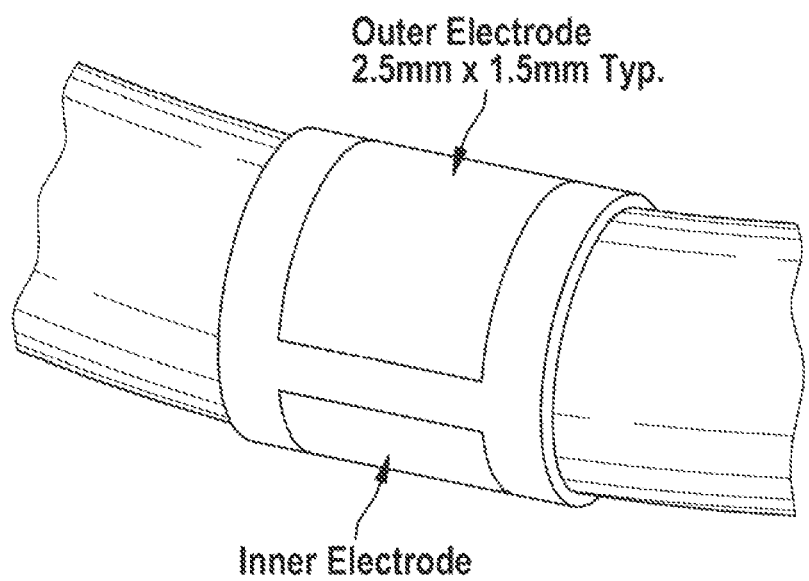

The above explained embodiments of ablation catheters realize IRE in order to prevent spread of electrical signals (i.e. achieve conduction block) that gives rise to the cardiac arrhythmia along a contiguous area with improved safety, as it is believed to spare adjacent tissues (e.g. nerves, vessels, esophagus), and with shorter ablation time. FIG. 17 illustrates such moat of conduction block, or electrical isolation. The right superior pulmonary vein 1701 is seen at the center of the picture. After application of PFA pulses according to this invention (totaling cumulative PFA application time of about 90 s/PV), a continuous, contiguous and transmural lesion was achieved. The lesion perimeter 1402 is illustrated. The moat of conduction block, or electrical isolation, 1403 completely covers the cardiac tissue zone between RSPV 1401 and the lesion border 1402. Electroanatomic mapping confirmed lasting chronic isolation of pulmonary veins. FIG. 18A shows the catheter of this invention facing a pulmonary vein atrium. FIG. 18B shows the catheter of this invention deployed when pressed against pulmonary vein wall. As indicated by line c1 and c2 the angular separation between the most distal electrode 1802 and the most proximal electrode 1801 exceeds 2*360°, or 720°. FIG. 18C shows an alternative split-tip electrode construction with an inner electrode facing the blood and an outer electrode facing the tissue.

Figure 19:
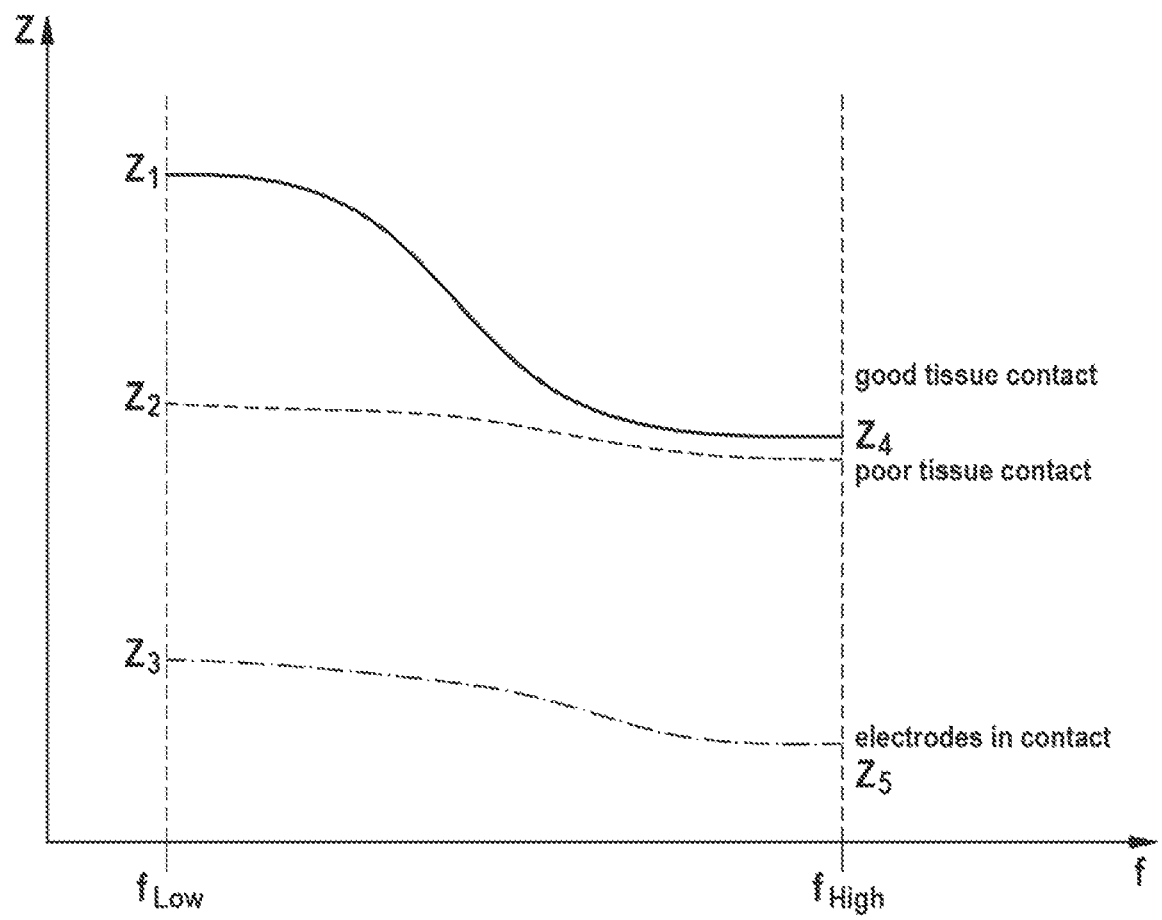
FIG. 19 shows three schematic impedance curves measured over frequency between two electrodes.

FIG. 19 shows three schematic impedance curves measured over frequency between two electrodes. The impedance could be measured starting with a low frequency $F_{LOW}$ of 10 kHz up to a frequency $F_{HIGH}$ of 500 kHz. A pronounced impedance curve as the topmost curve ranging from $Z_1$ to $Z_4$ indicates a good tissue contact between the two electrodes. A flat lowermost impedance curve in the lower range of $Z_3$ to $Z_5$ indicates contact between the two electrodes. The flat impedance curve in the middle ranging from $Z_2$ to $Z_4$ indicates bad tissue contact between the two electrodes. For example, without limitation, following thresholds may be used:

1. Good tissue contact—at $F_{LOW}$ (e.g. 10 kHz) $Z_1$ is in the range 100-500 ohm, depending on electrode size and tissue properties. At $F_{HIGH}$ (e.g. 500 kHz) $Z_4$ is at least 20% lower than $Z_1$ (S-curve).
2. Poor contact—at $F_{LOW}$ (e.g. 10 kHz) $Z_2$ is in the range of 80-400 ohm, depending on electrode size and blood properties. At $F_{HIGH}$ (e.g. 500 kHz) $Z_4$ is at most 20% lower than $Z_2$, typically only 10% or less lower (flat curve). As shown in FIG. 20A, under poor electrical contact conditions, the bipolar impedance decreases from about 113 ohm at 10 kHz to about 110 ohm at 500 kHz. The phase varies only slightly, increasing from about −4° to 2°.
3. Electrodes in contact—at $F_{LOW}$ (e.g. 10 kHz) $Z_3$ is in the range 0-300 ohm, depending on the amount of contact, electrode size, blood properties. At $F_{HIGH}$ (e.g. 500 kHz) $Z_5$ is at most 20% lower than $Z_3$, typically only 10% or less lower (flat curve). As shown in FIG. 20B, when electrodes collide and make good electrical contact, $Z_5$ is low, between 4-9 ohm, while phase increases with frequency. At 500 kHz, the phase is approximately 66°, indicating a mostly inductive electrical characteristic given by the electrode wires.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

What is claimed is:

1. A method for pulmonary vein isolation (PVI) treatment on heart tissue comprising:
providing an ablation catheter comprising an ablation portion having a plurality of electrodes at a distal end and a proximal end adapted to connect to an electronic control unit configured to provide monopolar, bipolar, or a combination of monopolar and bipolar energy to the electrodes, wherein the ablation portion comprises at least two loop sections forming a three dimensional spiral, wherein a distance between a first electrode on a first loop section and a second electrode on a second loop section and closest to the first electrode is greater than 2 mm and less than 5 mm in a compressed position where the ablation portion is flattened by an external force and less than 8 mm in an uncompressed position where the ablation portion is not restricted by any external force; and
energizing the plurality of electrodes with high voltage charge-balanced pulsed electric fields which are delivered in a monopolar arrangement.

2. The method of claim 1, wherein the high voltage charge-balanced pulsed electric fields are delivered in a combination of a monopolar arrangement and a bipolar arrangement.

3. The method of claim 2, wherein the first electrode and the second electrode are energized with said pulsed electric fields in a bipolar arrangement.

4. The method of claim 1, wherein the high voltage charge balanced pulsed electric field energy is applied in the form of biphasic pulses comprising a positive and a negative pulse section, whereby the charge of the positive section balances out the charge of the negative section.

5. The method of claim 4, wherein energizing the plurality of electrodes with high voltage charge-balanced pulsed electric fields comprises a biphasic pulse followed by an inverse biphasic pulse separated by an interphase delay within a range of 1 µs to 100 µs.

6. The method of claim 4, wherein a pulse shape of the biphasic pulses is an exponential-decay.

7. The method of claim 4, wherein a voltage amplitude of pulses delivered to said catheter electrodes is greater than 1 kV.

8. The method of claim 4, wherein a voltage amplitude of pulses delivered to said catheter electrodes is greater than 2.5 kV.

9. The method of claim 4, wherein a voltage amplitude of pulses delivered to said catheter electrodes is between 2.5 kV and 10 kV.

10. The method of claim 4, wherein a pulse width of pulses delivered to said catheter electrodes is greater than 0.5 µs.

11. The method of claim 4, wherein a pulse width of pulses delivered to said catheter electrodes is between 0.5 µs and 30 µs.

12. The method of claim 1, wherein energizing the plurality of electrodes with high voltage charge-balanced pulsed electric fields is synchronized to a QRS cycle, P wave and/or T wave.

13. The method of claim 1, wherein a sterile irrigation fluid is applied at a treatment site, whereby distilled water or a physiological saline solution having a salinity of no more than 0.1%, is used as irrigation fluid.

14. A method for pulmonary vein isolation (PVI) treatment on heart tissue comprising:
providing an ablation catheter comprising an ablation portion having a plurality of electrodes at a distal end and a proximal end adapted to connect to an electronic control unit configured to provide monopolar, bipolar, or a combination of monopolar and bipolar energy to the electrodes, wherein the ablation portion comprises at least two loop sections forming a three dimensional spiral, wherein a distance between a first electrode on a first loop section and a second electrode on a second loop section and closest to the first electrode is greater than 2 mm and less than 5 mm in a compressed position where the ablation portion is flattened by an external force and less than 8 mm in an uncompressed position where the ablation portion is not restricted by any external force; and
energizing the plurality of electrodes with high voltage charge balanced pulsed electric fields which are delivered in a bipolar arrangement.

15. The method of claim 14, wherein the first electrode and the second electrode are energized with said pulsed electric fields in a bipolar arrangement.

16. The method of claim 14, wherein the high voltage charge balanced pulsed electric field energy is applied in the form of biphasic pulses comprising a positive and a negative pulse section, whereby the charge of the positive section balances out the charge of the negative section.

17. The method of claim 16, wherein energizing the plurality of electrodes with high voltage charge-balanced pulsed electric fields comprises a biphasic pulse followed by an inverse biphasic pulse separated by an interphase delay within a range of 1 µs to 100 µs.

18. The method of claim 16, wherein a pulse shape of the biphasic pulses is an exponential-decay.

19. The method of claim 14, wherein energizing the plurality of electrodes with high voltage charge balanced pulsed electric fields is synchronized to a QRS cycle, P wave and/or T wave.

20. The method of claim 16, wherein a voltage amplitude of pulses delivered to said catheter electrodes is greater than 1 kV.

21. The method of claim 16, wherein a voltage amplitude of pulses delivered to said catheter electrodes is greater than 2.5 kV.

22. The method of claim 16, wherein a voltage amplitude of pulses delivered to said catheter electrodes is between 2.5 kV and 10 kV.

23. The method of claim 16, wherein a pulse width of pulses delivered to said catheter electrodes is greater than 0.5 µs.

24. The method of claim 16, wherein a pulse width of pulses delivered to said catheter electrodes is between 0.5 µs and 30 µs.

25. The method of claim 14, wherein a sterile irrigation fluid is applied at a treatment site, whereby distilled water or a physiological saline solution having a salinity of no more than 0.1%, is used as irrigation fluid.

* * * * *